US009783586B2

(12) United States Patent
Staudt et al.

(10) Patent No.: US 9,783,586 B2
(45) Date of Patent: Oct. 10, 2017

(54) INHIBITORS OF THE LINEAR UBIQUITIN CHAIN ASSEMBLY COMPLEX (LUBAC) AND RELATED METHODS

(71) Applicant: The United States of America, as represented by the Secretary, Department of Health and Human Services, Washington, DC (US)

(72) Inventors: Louis M. Staudt, Bethesda, MD (US); Yibin Yang, Rockville, MD (US); Federico Bernal, Gaithersburg, MD (US); Amanda L. Whiting, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/774,478

(22) PCT Filed: Mar. 11, 2014

(86) PCT No.: PCT/US2014/023006
§ 371 (c)(1),
(2) Date: Sep. 10, 2015

(87) PCT Pub. No.: WO2014/150350
PCT Pub. Date: Sep. 25, 2014

(65) Prior Publication Data
US 2016/0031957 A1 Feb. 4, 2016

Related U.S. Application Data

(60) Provisional application No. 61/789,064, filed on Mar. 15, 2013.

(51) Int. Cl.
| | | |
|---|---|---|
| *C07K 14/47* | (2006.01) |
| *G01N 33/574* | (2006.01) |
| *C12Q 1/68* | (2006.01) |
| *A61K 38/00* | (2006.01) |
| *C12N 9/00* | (2006.01) |
| *A61K 38/17* | (2006.01) |
| *A61K 45/06* | (2006.01) |
| *A61N 5/10* | (2006.01) |

(52) U.S. Cl.
CPC .......... *C07K 14/4703* (2013.01); *A61K 38/00* (2013.01); *A61K 38/1709* (2013.01); *A61K 45/06* (2013.01); *A61N 5/10* (2013.01); *C07K 14/4713* (2013.01); *C12N 9/93* (2013.01); *C12Q 1/68* (2013.01); *C12Y 304/19012* (2013.01); *G01N 33/57407* (2013.01)

(58) Field of Classification Search
None
See application file for complete search history.

(56) References Cited

U.S. PATENT DOCUMENTS

| 7,964,369 B2 | 6/2011 | Fathman et al. |
| 2009/0176713 A1* | 7/2009 | Tymianski ........... A61K 9/0019 514/1.1 |
| 2011/0144306 A1 | 6/2011 | Verdine et al. |
| 2012/0145544 A1 | 6/2012 | Iwai |

FOREIGN PATENT DOCUMENTS

| EP | 2 463 367 | 6/2012 |
| JP | 2009-184878 | * 8/2009 |

OTHER PUBLICATIONS

Abecasis et al., "An integrated map of genetic variation from 1,092 human genomes," *Nature*, 491 (7422), 56-65 (Nov. 1, 2012).
Alizadeh et al., "Distinct types of diffuse large B-cell lymphoma identified by gene expression profiling," *Nature*, 403 (6769), 503-511 (2000).
Bernal et al., "Reactivation of the p53 tumor suppressor pathway by a stapled p53 peptide," *J. Am. Chem. Soc.*, 129 (9), 2456-2457 (Mar. 2007), published online Feb. 7, 2007.
Davis et al., "Chronic active B-cell-receptor signaling in diffuse large B-cell lymphoma," *Nature*, 463 (7277), 88-92 (2010) author manuscript.
Davis et al., "Constitutive nuclear factor κB activity is required for survival of activated B cell-like diffuse large B cell lymphoma cells," *J. Exp. Med.*, 194 (12), 1861-1874 (2001).
Ferch et al., "Inhibition of MALT1 protease activity is selectively toxic for activated B cell-like diffuse large B cell lymphoma cells," *J. Exp. Med.*, 206 (11), 2313-2320 (2009).
Genbank Accession No. NP_060469.4 (printed 2015).
Geneseq Accession No. ABU70897 (2003).
Haas et al., "Recruitment of the linear ubiquitin chain assembly complex stabilizes the TNF-R1 signaling complex and is required for TNF-mediated gene induction," *Mol. Cell*, 36 (5), 831-844 (2009).
Hailfinger et al., "Essential role of MALT1 protease activity in activated B cell-like diffuse large B-cell lymphoma," *Proc. Natl. Acad. Sci. USA*, 106 (47), 19946-19951 (2009).
Hymowitz et al., "A20: From ubiquitin editing to tumor suppression," *Nat. Rev. Cancer*, 10 (5), 332-340 (2010).
International Preliminary Report on Patentability, Application No. PCT/US2014/023006, date issued Sep. 15, 2015.
International Search Report, Application No. PCT/US2014/023006, date mailed Jul. 30, 2014.
Iwai et al., "Linear polyubiquitination: A new regulator of NF-κB activation," *EMBO Rep.*, 10 (7), 706-713 (2009).

(Continued)

*Primary Examiner* — Satyanarayana R Gudibande
*Assistant Examiner* — Jia-Hai Lee
(74) *Attorney, Agent, or Firm* — Leydig, Voit & Mayer, Ltd.

(57) ABSTRACT

The invention relates to peptide inhibitors of linear ubiquitin chain assembly complex (LUBAC) and to methods of treating diseases including activated B-cell like diffuse large B cell lymphoma (ABC DLBCL) and autoimmune or inflammatory disorders.

40 Claims, 9 Drawing Sheets

(56) References Cited

OTHER PUBLICATIONS

Figure 1:
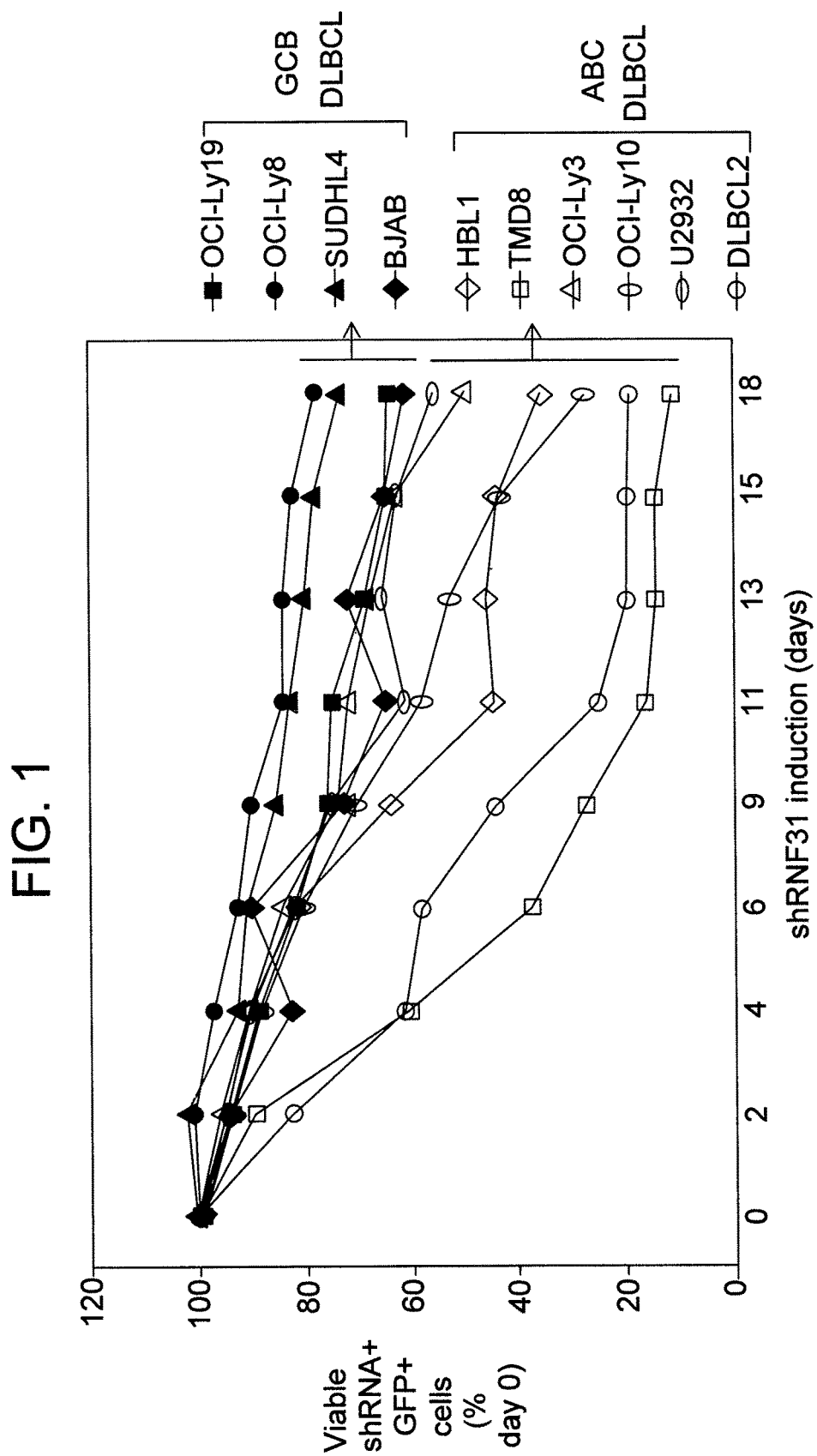

Kirisako et al., "A ubiquitin ligase complex assembles linear polyubiquitin chains," *EMBO J.*, 25 (20), 4877-4887 (2006).
Lam et al, "Small molecule inhibitors of IκB kinase are selectively toxic for subgroups of diffuse large B-cell lymphoma defined by gene expression profiling," *Clin. Cancer Res.*, 11 (1), 28-40 (2005).
Lam et al., "Cooperative signaling through the signal transducer and activator of transcription 3 and nuclear factor-κB pathways in subtypes of diffuse large B-cell lymphoma, " *Blood*, 111 (7), 3701-3713 (2008).
Lenz et al., "Molecular subtypes of diffuse large B-cell lymphoma arise by distinct genetic pathways," *Proc. Natl. Acad. Sci. USA*, 105 (36), 13520-13525 (2008).
Lenz et al., "Oncogenic CARD11 mutations in human diffuse large B cell lymphoma," *Science*, 319 (5870), 1676-1679 (2008).
Ngo et al., "Oncogenically active MYD88 mutations in human lymphoma," *Nature*, 470 (7332), 115-119 (2011).
Ngo et al., "A loss-of-function RNA interference screen for molecular targets in cancer," *Nature*, 441 (7089), 106-110 (2006).
Niu et al., "LUBAC regulates NF-κB activation upon genotoxic stress by promoting linear ubiquitination of NEMO," *EMBO J.*, 30 (18), 3741-3753 (2011).
Rieser et al., "Linear ubiquitination: a newly discovered regulator of cell signalling" Trends in Biochem. Sci., 38 (2), 94-102 (2013), published online Jan. 17, 2013.
Schmukle et al., "No one can whistle a symphony alone—How different ubiquitin linkages cooperate to orchestrate NF-κB activity," *J. Cell Sci.*, 125 (Pt. 3), 549-559 (Feb. 1, 2012).
Shaffer et al., "IRF4 addiction in multiple myeloma," *Nature*, 454 (7201), 226-231 (2008).
Shaffer et al., "Pathogenesis of human B cell lymphomas," *Annu. Rev. Immunol.*, 30, 565-610 (2012) published online Jan. 6, 2012.
Smit et al., "The E3 ligase HOIP specifies linear ubiquitin chain assembly through its RING-IBR-RING domain and the unique LDD extension," *EMBO J.*, 31 (19), 3833-3844 (Oct. 3, 2012) published online Aug. 3, 2012.
Staudt "Oncogenic activation of NF-κB," *Cold Spring Herb. Perspect. Biol.*, 2 (6), doi: 10.1101/cshperspect.a000109, (2010).
Stieglitz et al., "LUBAC synthesizes linear ubiquitin chains via a thioester intermediate," EMBO Rep., 13 (9), 840-846 (Sep. 2012) published online Jul. 13, 2012.
Tennessen et al., "Evolution and functional impact of rare coding variation from deep sequencing of human exomes," *Science*, 337 (6090), 64-69 (Jul. 6, 2012) published online May 17, 2012 (author manuscript).
Tokunaga et al., "Linear ubiquitination: A novel NF-κB regulatory mechanism for inflammatory and immune responses by the LUBAC ubiquitin ligase complex," *Endocrine J.*, 59 (8), 641-652 (2012) published online May 19, 2012.
Tokunaga et al., "SHARPIN is a component of the NFκB-activating linear ubiquitin chain assembly complex," *Nature*, 471 (4370), 633-636 (2011).
Tokunaga et al., "LUBAC, a novel ubiquitin ligase for linear ubiquitination, is crucial for inflammation and immune responses," *Microbes. Infect.*, 14 (7-8), 563-572 (July 2012) published online Jan. 25, 2012.
Tokunaga et al., "Involvement of linear polyubiquitylation of NEMO in NF-κB activation," *Nat. Cell Biol.*, 11 (2), 123-132 (2009).
Verdine et al., "Stapled Peptides for Intracellular Drug Targets" *Methods Enzymol.*, 503, 3-23 (2012).
Verhelst et al., "A20 inhibits LUBAC-mediated NF-κB activation by binding linear polyubiquitin chains via its zinc finger 7," *EMBO J.*, 31 (19), 3845-3855 (Oct. 3, 2012) published online Aug. 28, 2012.
Walensky et al., "Activation of apoptosis in vivo by a hydrocarbon-stapled BH3 helix," *Science*, 305 (5689), 1466-1470 (2004).
Written Opinion of the International Searching Authority, Application No. PCT/US2014/023006, date Jul. 30, 2014.
Yagi et al., "A non-canonical UBA-UBL interaction forms the linear-ubiquitin-chain assembly complex," *EMBO Rep.*, 13 (5), 462-468 (May 1, 2012).
Yang et al., "Exploiting synthetic lethality for the therapy of ABC diffuse large B cell lymphoma," *Cancer Cell*, 21 (6), 723-737 (Jun. 12, 2012).
Yang et al., "Essential role of the linear ubiquitin chain assembly complex in lymphoma revealed by rare germline polymorphisms," *Cancer Discov.*, 4 (4), 480-493 (2014).

* cited by examiner

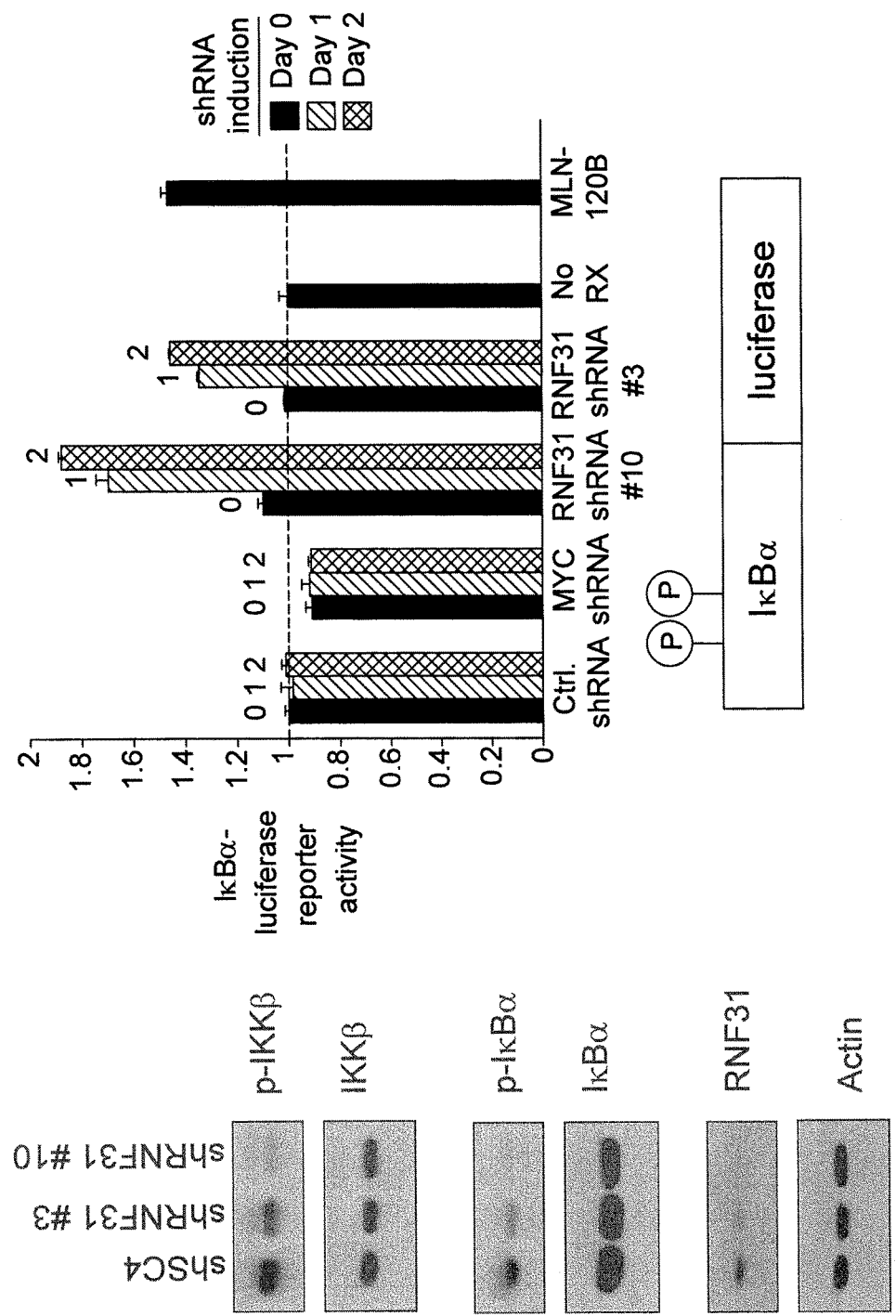
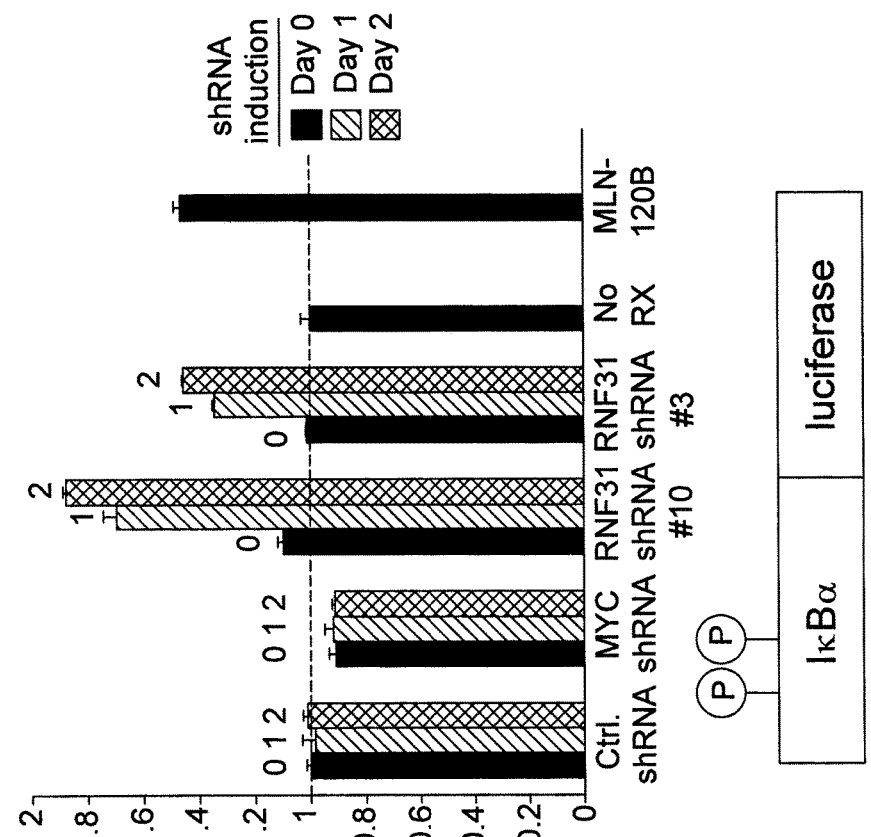

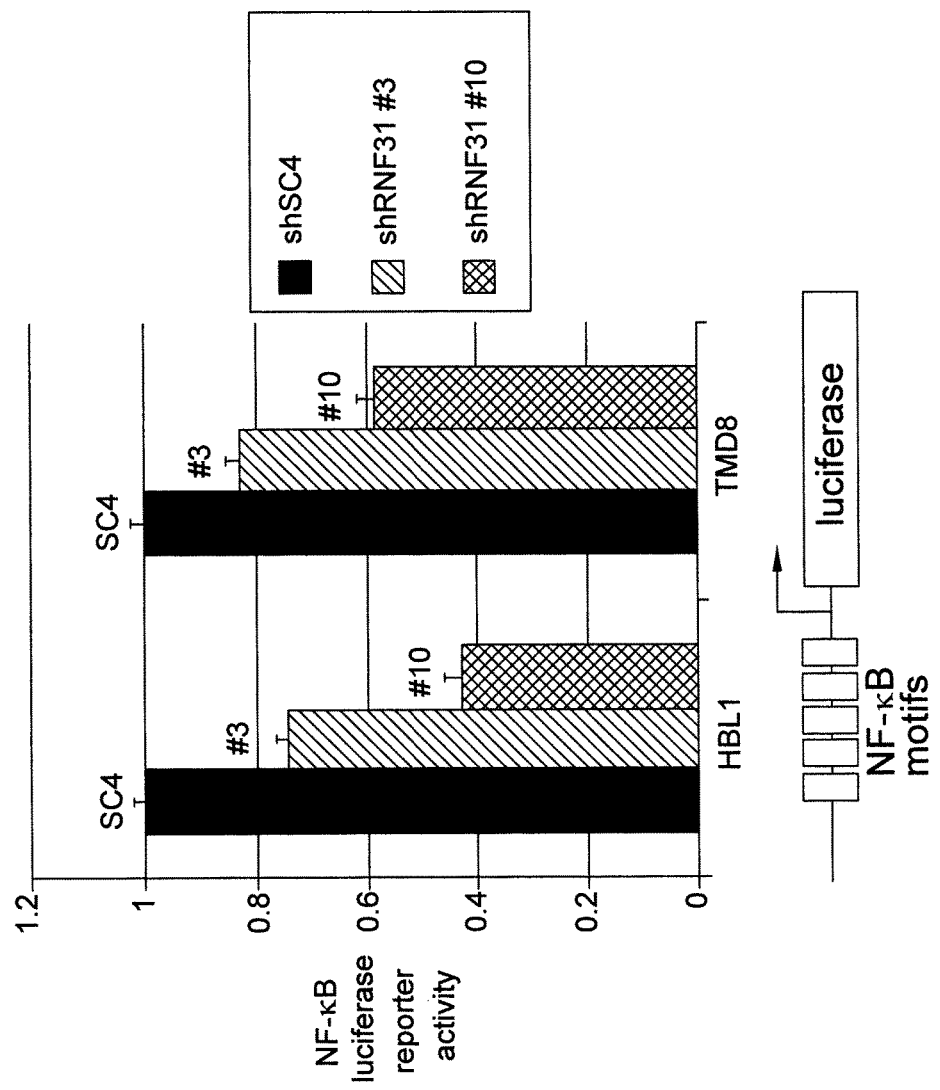

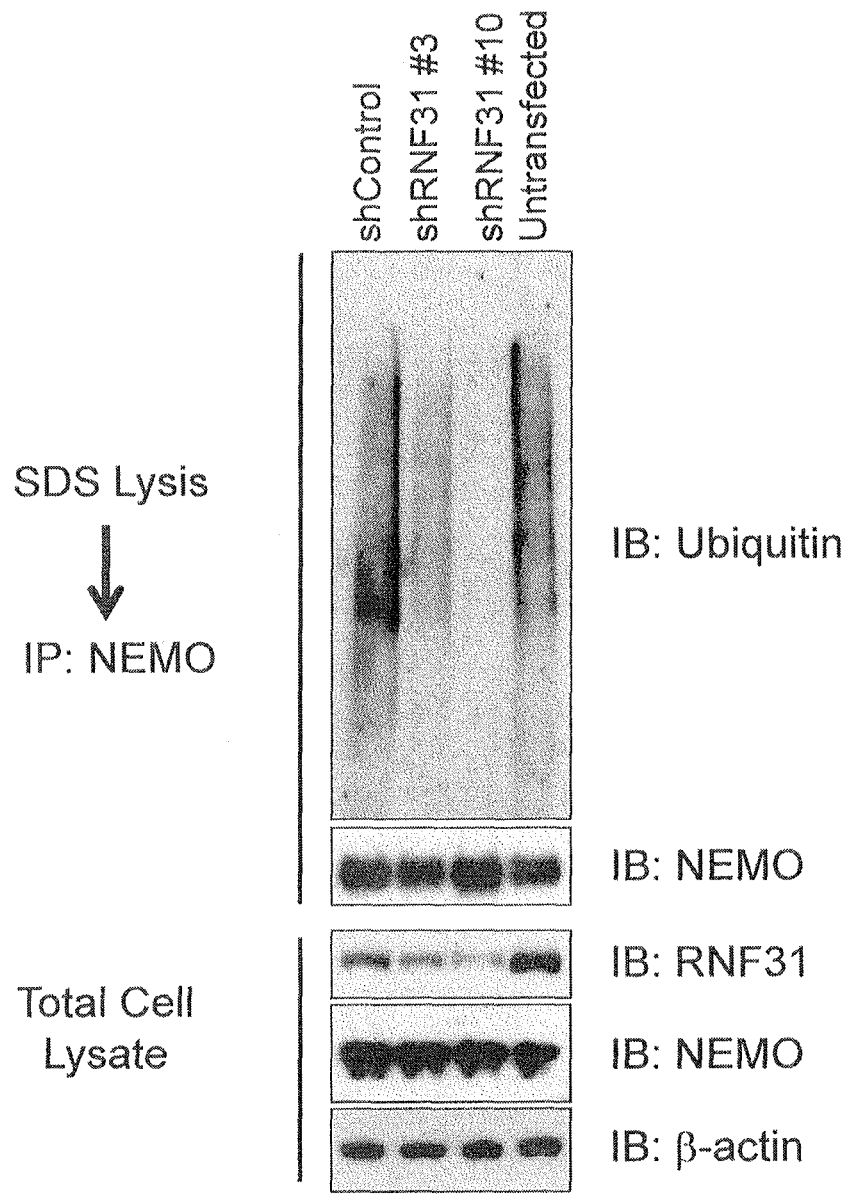

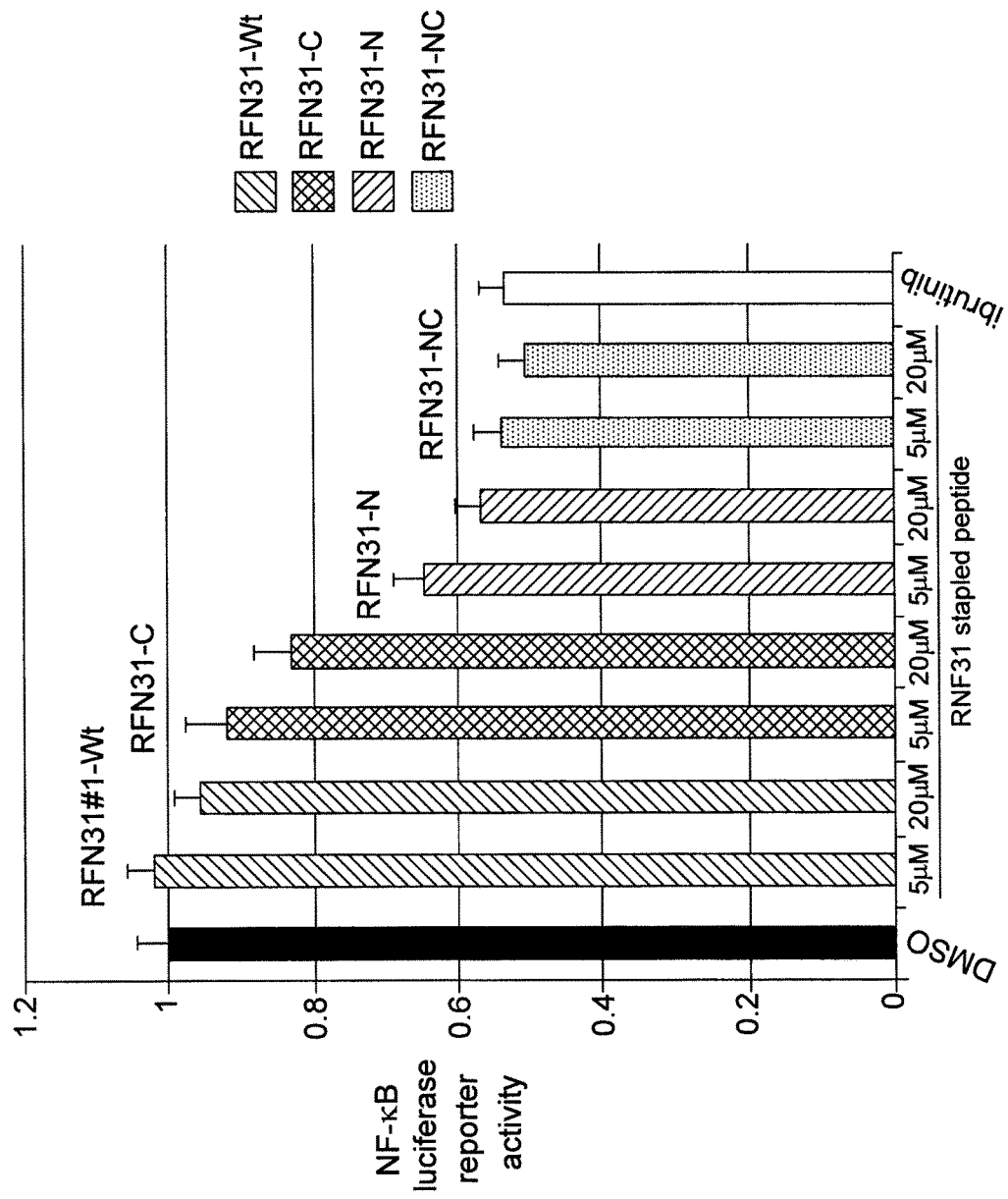

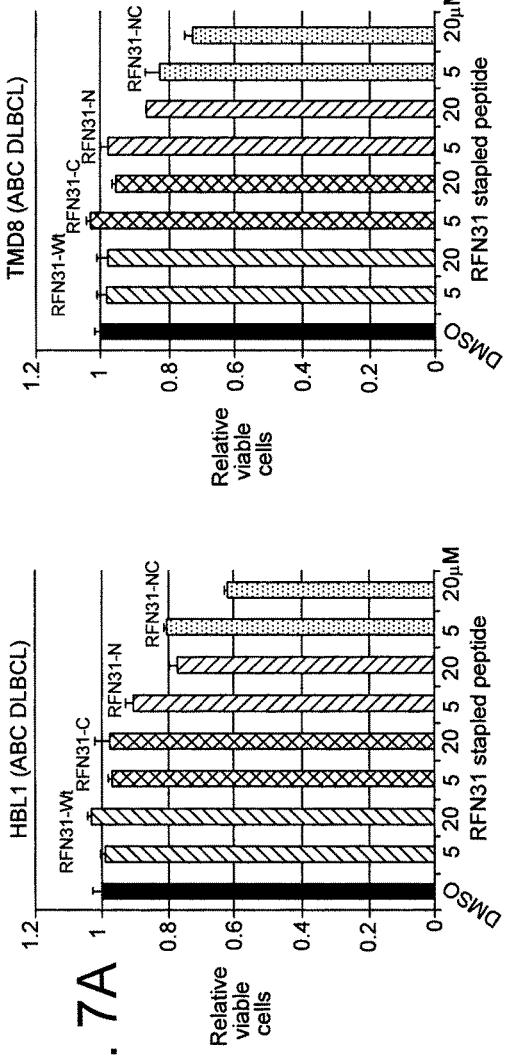
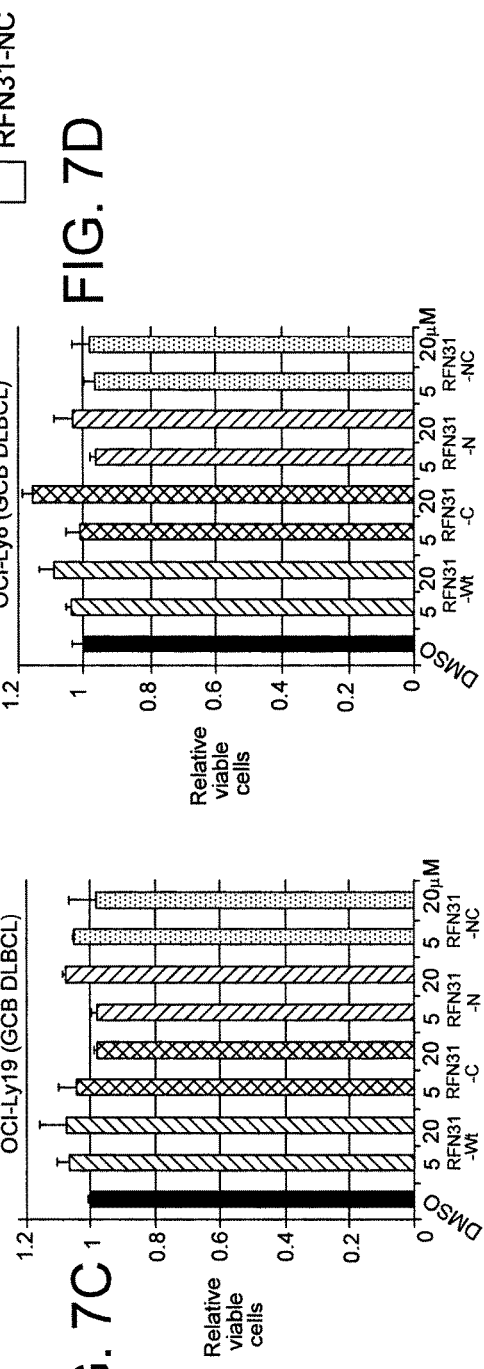
FIG. 7A, FIG. 7B, FIG. 7C, FIG. 7D

SEQUENCE LISTING

<160> NUMBER OF SEQ ID NOS: 20

<210> SEQ ID NO 1
<211> LENGTH: 23
<212> TYPE: PRT
<213> ORGANISM: Artificial Sequence
<220> FEATURE:
<223> OTHER INFORMATION: Synthetic

<400> SEQUENCE: 1

Ser Arg Ala Leu Thr Glu Leu Gln Arg Gln Arg Leu Glu Pro Phe Arg
1               5                   10                  15

Gln Arg Leu Trp Asp Ser Gly
            20

<210> SEQ ID NO 2

```
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Ser Arg Ala Leu Thr Glu Leu Gln Arg Gln Arg Leu Glu Pro Phe
1               5                   10                  15

Arg Gln Arg Leu Trp Asp Ser
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group
<220> FEATURE:
<221> NAME/KEY: MISC_FEATURE
<222> LOCATION: (20)..(20)
<223> OTHER INFORMATION: Xaa is a non-natural amino acid
<220> FEATURE:
<221> NAME/KEY: MISC_FEATURE
<222> LOCATION: (24)..(24)
<223> OTHER INFORMATION: Xaa is a non-natural amino acid
<220> FEATURE:
<221> NAME/KEY: MOD_RES
<222> LOCATION: (24)..(24)
<223> OTHER INFORMATION: carboxylic acid protecting group

<400> SEQUENCE: 3

Xaa Ser Arg Ala Leu Thr Glu Leu Gln Arg Gln Arg Leu Glu Pro Phe
1               5                   10                  15

Arg Gln Arg Xaa Trp Asp Ser Xaa
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group
<220> FEATURE:
<221> NAME/KEY: MISC_FEATURE
<222> LOCATION: (4)..(4)
<223> OTHER INFORMATION: Xaa is a non-natural amino acid
<220> FEATURE:
<221> NAME/KEY: MISC_FEATURE
<222> LOCATION: (8)..(8)
<223> OTHER INFORMATION: Xaa is a non-natural amino acid
<220> FEATURE:
<221> NAME/KEY: MOD_RES
```

<222> LOCATION: (23)..(23)
<223> OTHER INFORMATION: carboxylic acid protecting group

<400> SEQUENCE: 4

Xaa Ser Arg Xaa Leu Thr Glu Xaa Gln Arg Gln Arg Leu Glu Pro Phe
1               5                   10                  15

Arg Gln Arg Leu Trp Asp Ser
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group
<220> FEATURE:
<221> NAME/KEY: MISC_FEATURE
<222> LOCATION: (4)..(4)
<223> OTHER INFORMATION: Xaa is a non-natural amino acid
<220> FEATURE:
<221> NAME/KEY: MISC_FEATURE
<222> LOCATION: (8)..(8)
<223> OTHER INFORMATION: Xaa is a non-natural amino acid
<220> FEATURE:
<221> NAME/KEY: MISC_FEATURE
<222> LOCATION: (20)..(20)
<223> OTHER INFORMATION: Xaa is a non-natural amino acid
<220> FEATURE:
<221> NAME/KEY: MISC_FEATURE
<222> LOCATION: (24)..(24)
<223> OTHER INFORMATION: Xaa is a non-natural amino acid
<220> FEATURE:
<221> NAME/KEY: MOD_RES
<222> LOCATION: (24)..(24)
<223> OTHER INFORMATION: carboxylic acid protecting group

<400> SEQUENCE: 5

Xaa Ser Arg Xaa Leu Thr Glu Xaa Gln Arg Gln Arg Leu Glu Pro Phe
1               5                   10                  15

Arg Gln Arg Xaa Trp Asp Ser Xaa
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group
<220> FEATURE:
<221> NAME/KEY: MISC_FEATURE
<222> LOCATION: (4)..(4)
<223> OTHER INFORMATION: Xaa is a non-natural amino acid
<220> FEATURE:
<221> NAME/KEY: MISC_FEATURE
<222> LOCATION: (8)..(8)
<223> OTHER INFORMATION: Xaa is a non-natural amino acid
<220> FEATURE:

<221> NAME/KEY: MISC_FEATURE
<222> LOCATION: (20)..(20)
<223> OTHER INFORMATION: Xaa is a non-natural amino acid
<220> FEATURE:
<221> NAME/KEY: MISC_FEATURE
<222> LOCATION: (24)..(24)
<223> OTHER INFORMATION: Xaa is a non-natural amino acid
<220> FEATURE:
<221> NAME/KEY: MOD_RES
<222> LOCATION: (24)..(24)
<223> OTHER INFORMATION: carboxylic acid protecting group

<400> SEQUENCE: 6

Xaa Ser Arg Xaa Leu Thr Glu Xaa Gln Arg Gln Arg Leu Glu Gly Phe
1               5                   10                  15

Arg Gln Arg Xaa Trp Asp Ser Xaa
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group
<220> FEATURE:
<221> NAME/KEY: MISC_FEATURE
<222> LOCATION: (4)..(4)
<223> OTHER INFORMATION: Xaa is a non-natural amino acid
<220> FEATURE:
<221> NAME/KEY: MISC_FEATURE
<222> LOCATION: (8)..(8)
<223> OTHER INFORMATION: Xaa is a non-natural amino acid
<220> FEATURE:
<221> NAME/KEY: MISC_FEATURE
<222> LOCATION: (20)..(20)
<223> OTHER INFORMATION: Xaa is a non-natural amino acid
<220> FEATURE:
<221> NAME/KEY: MISC_FEATURE
<222> LOCATION: (24)..(24)
<223> OTHER INFORMATION: Xaa is a non-natural amino acid
<220> FEATURE:
<221> NAME/KEY: MOD_RES
<222> LOCATION: (24)..(24)
<223> OTHER INFORMATION: carboxylic acid protecting group

<400> SEQUENCE: 7

Xaa Ser Arg Xaa Leu Thr Glu Xaa Gln Arg Gln Arg Leu Glu Pro Phe
1               5                   10                  15

Arg Leu Arg Xaa Trp Asp Ser Xaa
            20

<210> SEQ ID NO 8
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group

```
<220> FEATURE:
<221> NAME/KEY: MISC_FEATURE
<222> LOCATION: (4)..(4)
<223> OTHER INFORMATION: Xaa is a non-natural amino acid
<220> FEATURE:
<221> NAME/KEY: MISC_FEATURE
<222> LOCATION: (8)..(8)
<223> OTHER INFORMATION: Xaa is a non-natural amino acid
<220> FEATURE:
<221> NAME/KEY: MISC_FEATURE
<222> LOCATION: (20)..(20)
<223> OTHER INFORMATION: Xaa is a non-natural amino acid
<220> FEATURE:
<221> NAME/KEY: MISC_FEATURE
<222> LOCATION: (24)..(24)
<223> OTHER INFORMATION: Xaa is a non-natural amino acid
<220> FEATURE:
<221> NAME/KEY: MOD_RES
<222> LOCATION: (24)..(24)
<223> OTHER INFORMATION: carboxylic acid protecting group

<400> SEQUENCE: 8

Xaa Ser Arg Xaa Leu Thr Glu Xaa Gln Arg Gln Arg Leu Glu Pro Phe
1               5                   10                  15

Cys Gln Arg Xaa Trp Asp Ser Xaa
            20

<210> SEQ ID NO 9
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group
<220> FEATURE:
<221> NAME/KEY: MISC_FEATURE
<222> LOCATION: (4)..(4)
<223> OTHER INFORMATION: Xaa is a non-natural amino acid
<220> FEATURE:
<221> NAME/KEY: MISC_FEATURE
<222> LOCATION: (8)..(8)
<223> OTHER INFORMATION: Xaa is a non-natural amino acid
<220> FEATURE:
<221> NAME/KEY: MISC_FEATURE
<222> LOCATION: (20)..(20)
<223> OTHER INFORMATION: Xaa is a non-natural amino acid
<220> FEATURE:
<221> NAME/KEY: MISC_FEATURE
<222> LOCATION: (24)..(24)
<223> OTHER INFORMATION: Xaa is a non-natural amino acid
<220> FEATURE:
<221> NAME/KEY: MOD_RES
<222> LOCATION: (24)..(24)
<223> OTHER INFORMATION: carboxylic acid protecting group

<400> SEQUENCE: 9

Xaa Ser Arg Xaa Leu Thr Glu Xaa Gln Arg Gln Arg Leu Glu Pro Phe
1               5                   10                  15

Cys Leu Arg Xaa Trp Asp Ser Xaa
            20

<210> SEQ ID NO 10
<211> LENGTH: 24
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (20)..(20)
<223> OTHER INFORMATION: Xaa is non-natural (S)-pentenylalanine
<220> FEATURE:
<221> NAME/KEY: MISC_FEATURE
<222> LOCATION: (24)..(24)
<223> OTHER INFORMATION: Xaa is non-natural (S)-pentenylalanine
<220> FEATURE:
<221> NAME/KEY: MOD_RES
<222> LOCATION: (24)..(24)
<223> OTHER INFORMATION: AMIDATION

<400> SEQUENCE: 10

Xaa Ser Arg Ala Leu Thr Glu Leu Gln Arg Gln Arg Leu Glu Pro Phe
1               5                   10                  15

Arg Gln Arg Xaa Trp Asp Ser Xaa
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa is non-natural (S)-pentenylalanine
<220> FEATURE:
<221> NAME/KEY: MISC_FEATURE
<222> LOCATION: (8)..(8)
<223> OTHER INFORMATION: Xaa is non-natural (S)-pentenylalanine
<220> FEATURE:
<221> NAME/KEY: MOD_RES
<222> LOCATION: (23)..(23)
<223> OTHER INFORMATION: AMIDATION

<400> SEQUENCE: 11

Xaa Ser Arg Xaa Leu Thr Glu Xaa Gln Arg Gln Arg Leu Glu Pro Phe
1               5                   10                  15

Arg Gln Arg Leu Trp Asp Ser
            20

<210> SEQ ID NO 12
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
```

<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa is non-natural (S)-pentenylalanine
<220> FEATURE:
<221> NAME/KEY: MISC_FEATURE
<222> LOCATION: (8)..(8)
<223> OTHER INFORMATION: Xaa is non-natural (S)-pentenylalanine
<220> FEATURE:
<221> NAME/KEY: MISC_FEATURE
<222> LOCATION: (20)..(20)
<223> OTHER INFORMATION: Xaa is non-natural (S)-pentenylalanine
<220> FEATURE:
<221> NAME/KEY: MISC_FEATURE
<222> LOCATION: (24)..(24)
<223> OTHER INFORMATION: Xaa is non-natural (S)-pentenylalanine
<220> FEATURE:
<221> NAME/KEY: MOD_RES
<222> LOCATION: (24)..(24)
<223> OTHER INFORMATION: AMIDATION

<400> SEQUENCE: 12

Xaa Ser Arg Xaa Leu Thr Glu Xaa Gln Arg Gln Arg Leu Glu Pro Phe
1               5                   10                  15

Arg Gln Arg Xaa Trp Asp Ser Xaa
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa is non-natural (S)-pentenylalanine
<220> FEATURE:
<221> NAME/KEY: MISC_FEATURE
<222> LOCATION: (8)..(8)
<223> OTHER INFORMATION: Xaa is non-natural (S)-pentenylalanine
<220> FEATURE:
<221> NAME/KEY: MISC_FEATURE
<222> LOCATION: (20)..(20)
<223> OTHER INFORMATION: Xaa is non-natural (S)-pentenylalanine
<220> FEATURE:
<221> NAME/KEY: MISC_FEATURE
<222> LOCATION: (24)..(24)
<223> OTHER INFORMATION: Xaa is non-natural (S)-pentenylalanine
<220> FEATURE:
<221> NAME/KEY: MOD_RES
<222> LOCATION: (24)..(24)
<223> OTHER INFORMATION: AMIDATION

<400> SEQUENCE: 13

Xaa Ser Arg Xaa Leu Thr Glu Xaa Gln Arg Gln Arg Leu Glu Gly Phe
1               5                   10                  15

Arg Gln Arg Xaa Trp Asp Ser Xaa
            20

<210> SEQ ID NO 14
<211> LENGTH: 24
<212> TYPE: PRT

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa is non-natural (S)-pentenylalanine
<220> FEATURE:
<221> NAME/KEY: MISC_FEATURE
<222> LOCATION: (8)..(8)
<223> OTHER INFORMATION: Xaa is non-natural (S)-pentenylalanine
<220> FEATURE:
<221> NAME/KEY: MISC_FEATURE
<222> LOCATION: (20)..(20)
<223> OTHER INFORMATION: Xaa is non-natural (S)-pentenylalanine
<220> FEATURE:
<221> NAME/KEY: MISC_FEATURE
<222> LOCATION: (24)..(24)
<223> OTHER INFORMATION: Xaa is non-natural (S)-pentenylalanine
<220> FEATURE:
<221> NAME/KEY: MOD_RES
<222> LOCATION: (24)..(24)
<223> OTHER INFORMATION: AMIDATION

<400> SEQUENCE: 14

Xaa Ser Arg Xaa Leu Thr Glu Xaa Gln Arg Gln Arg Leu Glu Pro Phe
1               5                   10                  15

Arg Leu Arg Xaa Trp Asp Ser Xaa
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa is non-natural (S)-pentenylalanine
<220> FEATURE:
<221> NAME/KEY: MISC_FEATURE
<222> LOCATION: (8)..(8)
<223> OTHER INFORMATION: Xaa is non-natural (S)-pentenylalanine
<220> FEATURE:
<221> NAME/KEY: MISC_FEATURE
<222> LOCATION: (20)..(20)
<223> OTHER INFORMATION: Xaa is non-natural (S)-pentenylalanine
<220> FEATURE:
<221> NAME/KEY: MISC_FEATURE
<222> LOCATION: (24)..(24)
<223> OTHER INFORMATION: Xaa is non-natural (S)-pentenylalanine
<220> FEATURE:
<221> NAME/KEY: MOD_RES
<222> LOCATION: (24)..(24)
<223> OTHER INFORMATION: AMIDATION

<400> SEQUENCE: 15

Xaa Ser Arg Xaa Leu Thr Glu Xaa Gln Arg Gln Arg Leu Glu Pro Phe

```
                1               5                      10                     15
Cys Gln Arg Xaa Trp Asp Ser Xaa
                20
```

<210> SEQ ID NO 16
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa is non-natural (S)-pentenylalanine
<220> FEATURE:
<221> NAME/KEY: MISC_FEATURE
<222> LOCATION: (8)..(8)
<223> OTHER INFORMATION: Xaa is non-natural (S)-pentenylalanine
<220> FEATURE:
<221> NAME/KEY: MISC_FEATURE
<222> LOCATION: (20)..(20)
<223> OTHER INFORMATION: Xaa is non-natural (S)-pentenylalanine
<220> FEATURE:
<221> NAME/KEY: MISC_FEATURE
<222> LOCATION: (24)..(24)
<223> OTHER INFORMATION: Xaa is non-natural (S)-pentenylalanine

<400> SEQUENCE: 16

```
Xaa Ser Arg Xaa Leu Thr Glu Xaa Gln Arg Gln Arg Leu Glu Pro Phe
1               5                      10                     15
Cys Leu Arg Xaa Trp Asp Ser Xaa
                20
```

<210> SEQ ID NO 17
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is bAla
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa is non-natural (S)-pentenylalanine
<220> FEATURE:
<221> NAME/KEY: MISC_FEATURE
<222> LOCATION: (8)..(8)
<223> OTHER INFORMATION: Xaa is non-natural (S)-pentenylalanine
<220> FEATURE:
<221> NAME/KEY: MISC_FEATURE
<222> LOCATION: (20)..(20)
<223> OTHER INFORMATION: Xaa is non-natural (S)-pentenylalanine
<220> FEATURE:
<221> NAME/KEY: MISC_FEATURE
<222> LOCATION: (24)..(24)
<223> OTHER INFORMATION: Xaa is non-natural (S)-pentenylalanine
<220> FEATURE:
<221> NAME/KEY: MOD_RES
<222> LOCATION: (24)..(24)

```
<223> OTHER INFORMATION: AMIDATION

<400> SEQUENCE: 17

Xaa Ser Arg Xaa Leu Thr Glu Xaa Ala Arg Gln Arg Ala Glu Pro Ala
1               5                   10                  15

Arg Gln Arg Xaa Trp Asp Ser Xaa
            20

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
gaagacaagg ttgaagatga t                                         21

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
gagcgcagcc ttgcctctta c                                         21

<210> SEQ ID NO 20
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MOD_RES
<222> LOCATION: (1)..(1)
<223> OTHER INFORMATION: amino protecting group
<220> FEATURE:
<221> NAME/KEY: MOD_RES
<222> LOCATION: (24)..(24)
<223> OTHER INFORMATION: carboxylic acid protecting group

<400> SEQUENCE: 20

Xaa Ser Arg Ala Leu Thr Glu Leu Gln Arg Gln Arg Leu Glu Pro Phe
1               5                   10                  15

Arg Gln Arg Leu Trp Asp Ser Gly
            20
```

INHIBITORS OF THE LINEAR UBIQUITIN CHAIN ASSEMBLY COMPLEX (LUBAC) AND RELATED METHODS

CROSS-REFERENCE TO RELATED APPLICATIONS

This patent application is a U.S. National Phase of International Patent Application No. PCT/US2014/023006, filed Mar. 11, 2014, which claims the benefit of U.S. Provisional Patent Application No. 61/789,064, filed Mar. 15, 2013, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 14,842 Byte ASCII (Text) file named "721641 SequenceListing_ST25.TXT," created on Mar. 1, 2017.

BACKGROUND OF THE INVENTION

The linear ubiquitin chain assembly complex (LUBAC) includes three protein subunits: HOIP (also known as RNF31), HOIL-1L (also known as RBCK1), and SHARPIN. Niu et al., *EMBO J.*, 30:3741-3753 (2011). LUBAC catalyzes the formation of head-to-tail linear ubiquitin polymers and has been linked to the activation of canonical nuclear factor kappa B (NF-κB) signaling. Tokunaga et al., *Nature Cell Biol.*, 11: 123-132 (2009). Other ubiquitin chains, e.g., K63 linked chains, have been shown to regulate NF-κB activation in response to certain stimuli, including antigen stimulation of lymphocytes and TNF-α therapy. LUBAC and K63 ubiquitin chains appear to function differently and have different roles in NF-κB signaling. Iwai et al., *EMBO Reports*, 10: 706-713 (2009) ("Iwai et al.").

NF-κB refers to a family of homo and heterodimer transcription factors that integrate and coordinate signals from infectious and inflammatory agents and generate specific responses in a variety of cell types. Hymowitz et al., *Nature Reviews Cancer*, 10: 332-340 (2010). In their inactive resting state, NF-κB proteins are bound by inhibitory proteins ("IκBs") that sequester NF-κB in the cytoplasm and prevent its translocation to nucleus. The canonical NF-κB pathway is activated in response to specific stimuli (e.g., pro-inflammatory cytokines or infectious agents) and involves the activation of IκB kinase ("IKK") which is composed of several subunits, including a mater regulatory subunit referred to as NF-κB essential modulator (NEMO). IKK phosphorylates IκBs leading to the degradation of IκBs and release of NF-κB for translocation to the nucleus where NF-κB induces expression of stimulus-specific genes. See, e.g., Iwai et al. (2009).

Many diseases, including cancer, involve dysregulated NF-κB signaling. Given the complexity of signaling pathways that converge on NF-κB, there is a desire to understand how NF-κB activity is dysregulated in these disease states. There is also a desire to develop therapeutic agents which are useful in the treatment of NF-κB dysregulated diseases.

BRIEF SUMMARY OF THE INVENTION

The invention is based, in part, on the discovery of peptide inhibitors of the linear ubiquitin chain assembly complex (LUBAC). The peptide inhibitors are based on the sequence of Ser Arg Ala Leu Thr Glu Leu Gln Arg Gln Arg Leu Glu Pro Phe Arg Gln Arg Leu Tip Asp Ser Gly (SEQ ID NO: 1) and include modified variants thereof, such as, peptides comprising sequences of SEQ ID NOs: 2-16. These peptide inhibitors can be used to treat diseases that require LUBAC activation of NF-κB signaling.

In another aspect, the invention is based, in part, on the discovery that LUBAC inhibitors are selectively cytotoxic to activated B-cell like diffuse large B cell lymphoma (ABC DLBCL). Thus, the invention provides a method of killing ABC DLBCL cells that includes administering a LUBAC inhibitor to the ABC DLBCL. The invention provides a method of treating a patient suffering from or at risk for ABC DLBCL that includes administering a pharmaceutical composition comprising a LUBAC inhibitor to the patient. In certain embodiments, the treatment method includes administering a pharmaceutical composition comprising a peptide inhibitor comprising the sequence of any one of SEQ ID NOs: 1-16 to a patient suffering from or at risk for ABC DLBCL. In particular embodiments, the treatment method further includes co-administering a second therapeutic agent to such a patient. For example, the peptide inhibitor can be administered in combination with a cytotoxic agent used in a chemotherapeutic regimen or in combination with a radiological agent used in a radiation therapy regimen.

BRIEF DESCRIPTION OF THE DRAWING(S)

FIG. 1 is a graph illustrating that shRNA depletion of RNF31 (HOIP) is cytotoxic for ABC DLBCL but not GCB DLBCL as determined by shRNA toxicity and complementation assays. Number of viable cells remaining (expressed as percentage of initially viable cells before induction of shRNA) is indicated on the y-axis, and the number of days following inducement of shRNA is indicated on the x-axis.

Figure 2D:
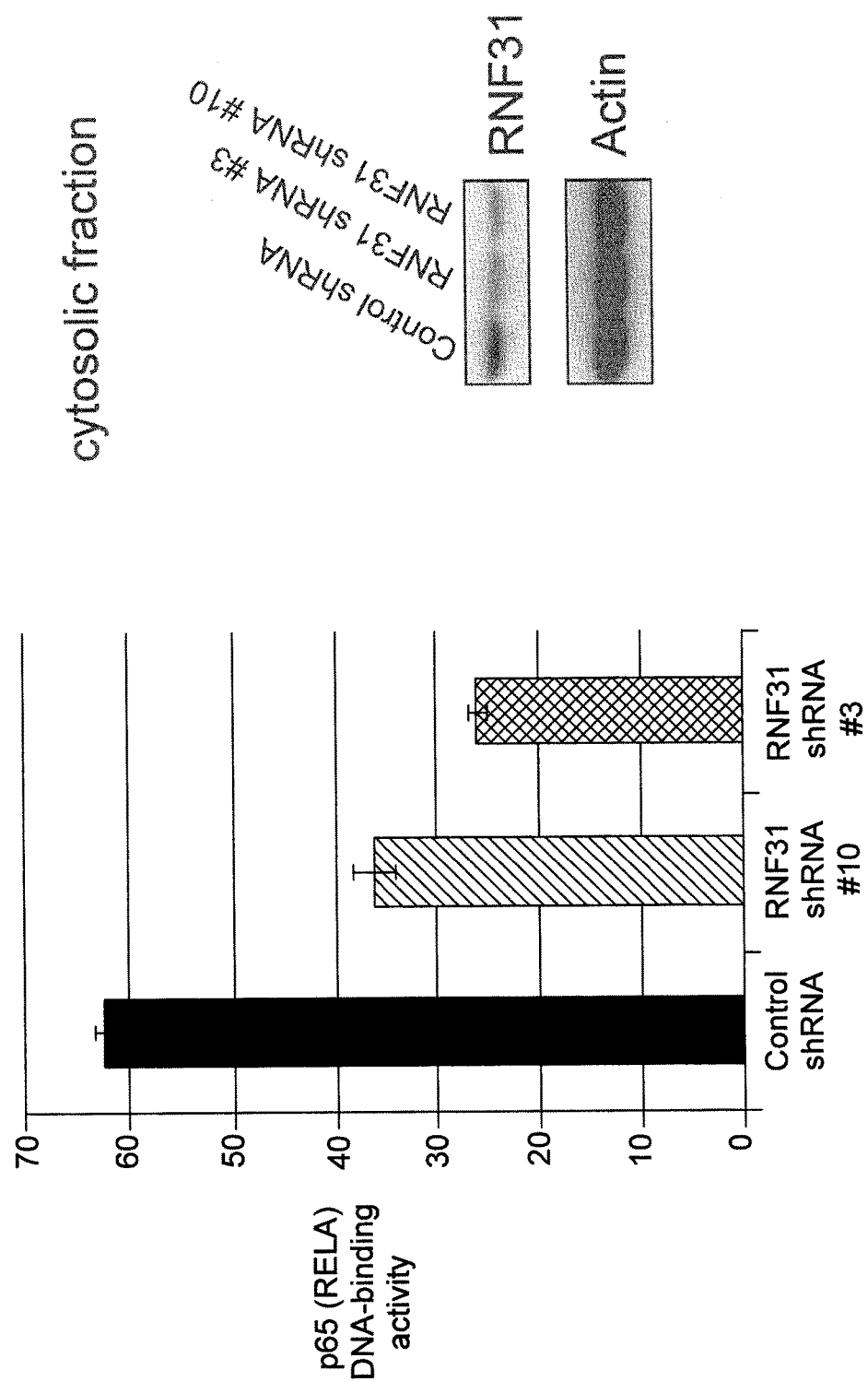

FIGS. 2A-2D illustrate that shRNA depletion of RNF31 disrupts NF-κB signaling in ABC DLBCL. FIG. 2A is a series of immmunoblot images showing the levels of the indicated proteins in ABC DLBCL cell lines expressing indicated shRNAs. FIG. 2B is a graph depicting the IκBα-reporter activity (y-axis) in ABC DLBCL cell lines expressing the shRNAs or treated with the reagents indicated on the x-axis; number of days after shRNA induction is indicated in the legend and above graph bars. FIG. 2C is a graph depicting NF-κB-reporter activity (y-axis) in the ABC DLBCL cell lines indicated on the x-axis, each expressing the shRNAs indicated in the legend and above graph bars. FIG. 2D includes a graph depicting NF-κB DNA binding activity (y-axis) in ABC DLBCL cell lines expressing the shRNAs indicated on the x-axis. FIG. 2D also includes two immmunoblot images showing the levels of the indicated proteins in cytosolic fractions from the same cell lines indicated in the graph of FIG. 2D.

FIG. 3 is a series of immmunoblot images. The two upper images show NEMO that was immunoprecipitated from ABC DLBCL cell lines expressing indicated shRNAs: ubiquitinated NEMO (IB: ubiquitin) and total NEMO (IB: NEMO) are shown. The three lower images show levels of the indicated proteins in total cell lysates.

FIG. 4 is a graph depicting NF-κB-reporter activity (y-axis) in ABC DLBCL cell lines expressing the shRNAs indicated in the legend and above graph bars. Cells were treated with the stapled peptides or reagents indicated on the x-axis.

Figure 5:
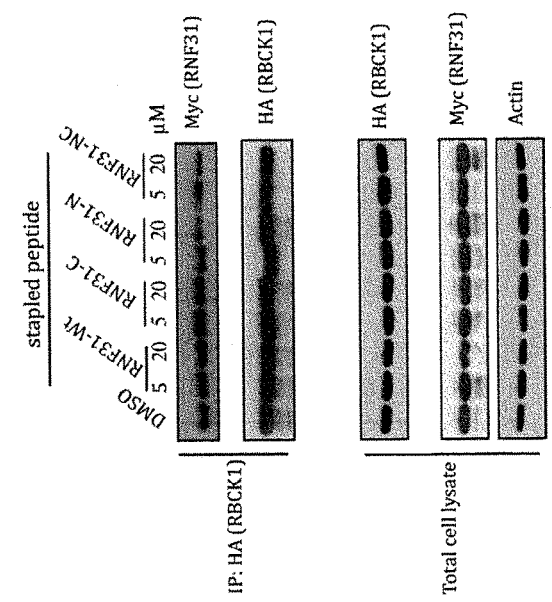

FIG. 5 is a series of immmunoblot images. The upper two images depict the amount of RNF 31 (tagged with MYC) and RBCK1 (tagged with HA) that was immunoprecipitated (using anti-HA antibody) from ABC DLBCL cell lines treated with the reagents or stapled peptides indicated above the immunoblot images. The two lower immunoblot images depict the levels of MYC-tagged RNF 31, HA-tagged RBCK1, and actin in total cell lysates.

Figure 6:
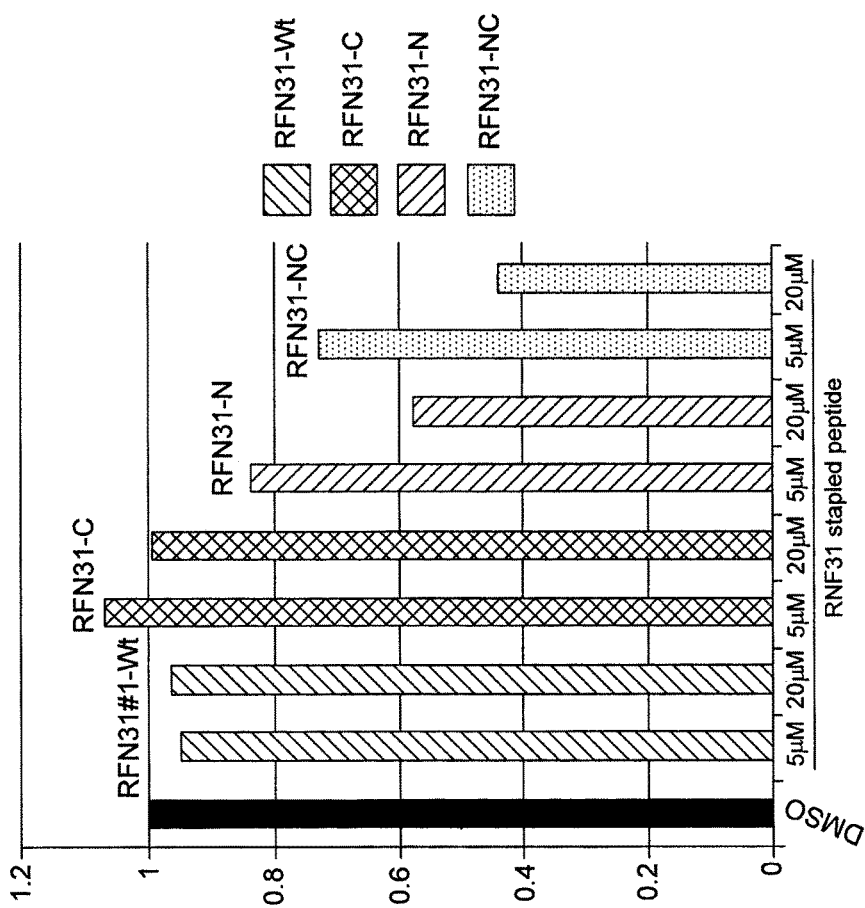

FIG. 6 is a graph depicting RNF 31-RBCK1 binding (y-axis) in ABC DLBCL cell lines treated with DMSO or each of the stapled peptides (indicated in the legend and above graph bars) at the dose concentrations indicated on the x-axis. Relative binding is expressed as a fraction of RNF 31-RBCK1 binding observed in DMSO-treated cells.

FIGS. 7A-7D are graphs depicting the results of cytotoxicity (MTS) assays done in each of the cell lines indicated at the top of each graph. In each graph, the y-axis shows the number of viable ABC DLBCL cells remaining after treatment with DMSO or the stapled peptides (indicated in the legend and above or below graph bars) at the dose concentrations indicated on the x-axis. Remaining viable cells (y-axis) is expressed as fraction of the initial number of viable cells before treatment.

Figure 8A:
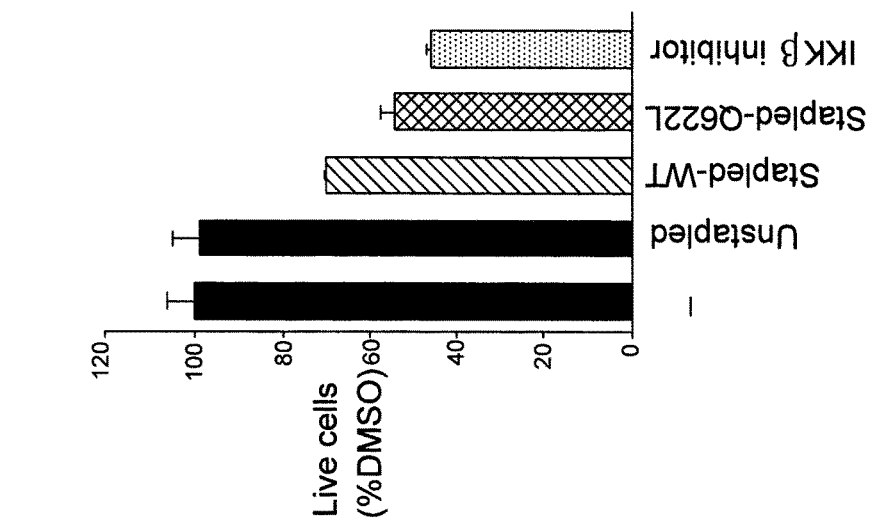
Figure 8B:
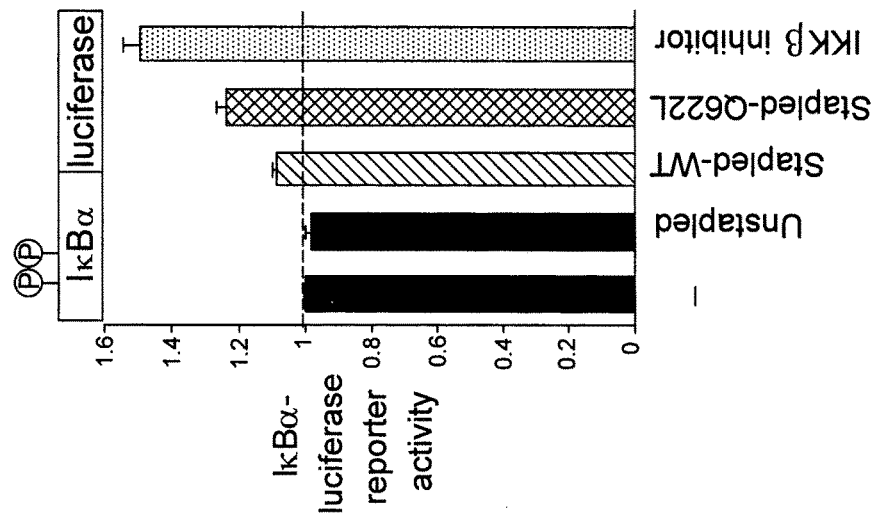
Figure 8C:
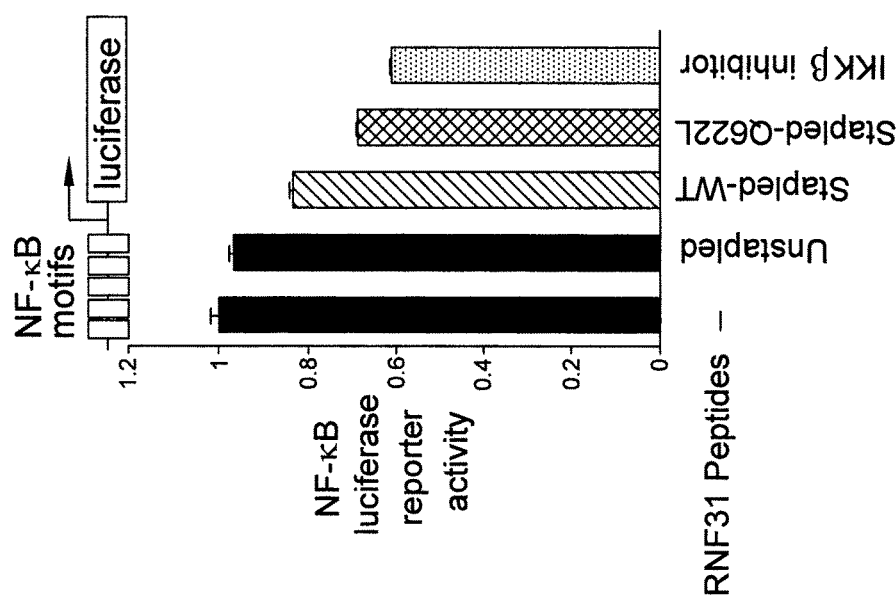

FIG. 8 is a series of three graphs showing the results of NF-κB-reporter activity assay (FIG. 8A), IκBα-reporter activity assay (FIG. 8B), and cytotoxicity (MTS) assay. Unstapled and stapled peptides used in each assay are indicated on the x-axis. The y-axes in FIGS. 8A, 8B, and 8C are the same as those described above for FIGS. 2C, 2B, and 1, respectively.

DETAILED DESCRIPTION OF THE INVENTION

In one aspect, the invention is based on the discovery of short peptide inhibitors of linear ubiquitin chain assembly complex (LUBAC). The peptide inhibitors of the invention can be used to disrupt LUBAC activity in vitro or in vivo. Moreover, the peptides of the invention can be used to inhibit LUBAC-mediated cell signaling, e.g., NF-κB signaling. Since LUBAC-mediated cell signaling is specific to certain cell types, the peptide inhibitors of the invention can be used to selectively inhibit LUBAC-mediated signaling, e.g., NF-κB signaling in specific cells.

The peptide inhibitors of the invention are based on the sequence of RNF31 (HOIP) at positions 606-628: Ser Arg Ala Leu Thr Glu Leu Gln Arg Gln Arg Leu Glu Pro Phe Arg Gln Arg Leu Trp Asp Ser Gly (SEQ ID NO: 1). This sequence corresponds to a portion of an α-helix domain located in the ubiquitin-associated domain ("UBA") domain of RNF31 (accession number NP_060469.4; GI:109150431). This UBA domain, including amino acids at about positions 556-636 of RNF31, has been reported to interact with the ubiquitin-associated domain ("UBL") domain of RBCK1 (HOIL-1L) and to be required for LUBAC complex formation. Kirisako et al., *EMBO J.*, 25, 4877-4887 (2006). It has been reported that, when isolated from other domains in RNF31, larger fragments of RNF31 containing the UBA domain (provided in trans) were ineffective and failed to inhibit LUBAC ligase activity in vitro and in vivo. Stieglitz et al., *EMBO Reports*, 13: 840-846 (2012) at 842 and Smit et al., *EMBO J.*, 31: 3833-3844 (2012) at 3835. In view of these findings, the invention provides small peptides that unexpectedly inhibit LUBAC activity and LUBAC-mediated NF-κB signaling.

In certain embodiments, a peptide inhibitor of the invention can be modified to include one or more protective groups, e.g., an amino-terminus protective group or a carboxylic acid protective group. Additionally, a peptide inhibitor according to the invention can include a spacer such as β-alanine or N-β-Fmoc-β-alanine located between the amino-terminus protective group and the first amino acid position corresponding to RNF31 (HOIP)-derived sequence.

In one embodiment, the peptide of the invention is a modified peptide as follows: Ac-βAla Ser Arg Ala Leu Thr Glu Leu Gln Arg Gln Arg Leu Glu Pro Phe Arg Gln Arg Leu Trp Asp Ser-NH2 (SEQ ID NO:2). This peptide includes the amino acid sequence of SEQ ID NO: 1, which is modified by an acetyl (Ac) cap and a β-alanine spacer at the N-terminus. This peptide is also amidated on the C-terminus.

In other embodiments, the amino acid sequence of SEQ ID NO: 1, e.g., in the foregoing modification of SEQ ID NO: 2, can be modified to include one, two, three, or four substitutions, deletions, or insertions. For example, the sequence of SEQ ID NO: 2 can be modified at one or more of amino acid positions 1, 3, 4, 6, 8, 10, 11, 17, 18, 20, 21, and 24.

In additional embodiments, the peptide inhibitor of the invention is a hydrocarbon-stapled α-helical peptide. Methods of making hydrocarbon stapled peptides are known in the art and have been described. See, e.g., Verdine et al., "Stapled Peptides for Intracellular Drug Targets" in *Methods in Enzymology*, 503: 3-23 (2012), which is incorporated herein by reference in its entirety. Generally, a stapled peptide refers to a peptide that includes at least one pair of non-natural (non-proteogenic) amino acids that are covalently cross-linked to each other and thereby form a hydrocarbon "staple" within the peptide. Such internal cross-links can function as "braces" or "locks" that stabilize the α-helical conformation of a peptide and/or improves cell penetration, target affinity, proteolytic resistance, or serum half-life of the peptide.

In certain embodiments, the peptide inhibitor of the invention comprises the sequence of SEQ ID NO: 1, which has been modified to include one, two, three, or four hydrocarbon staples. In certain embodiments, the peptides of the invention are cell-permeable or cell penetrating and therefore, useful for inhibiting LUBAC in vitro (e.g., in cells cultures, tissue cultures, or explants) or in vivo (e.g. in a subject).

In certain embodiments, the peptide inhibitor of the invention includes no more than 45 amino acids (a.a.). For example, the peptide inhibitor of the invention can include 44 a.a., 43 a.a., 42 a.a., 41 a.a., 40 a.a., 39 a.a., 38 a.a., 37 a.a., 36 a.a., 35 a.a., 34 a.a., 33 a.a., 32 a.a., 31 a.a., 30 a.a., 29 a.a., 28 a.a., 27 a.a., 26 a.a., 25 a.a., 24 a.a., or 23 a.a. Each of the foregoing numbers of amino acids "in length" refers only to the length of natural and non-natural amino acids included in a peptide of the invention. As used herein, a peptide of the invention is considered to be 45 amino acids in length both with and without additional non-amino acid constituents (e.g., with or without added N-terminal and/or C-terminal protective groups).

Stapled peptides according to the invention can include a hydrocarbon staple located near the N-terminus of the peptide. For example, a stapled peptide according to the invention can include a first non-natural amino acid substitution at position 3 of SEQ ID NO: 1 or position 4 of SEQ ID NO: 2 (replacing the alanine located between arginine and leucine residues). The first non-natural amino acid can be cross-linked to a second non-natural amino acid that is substituted or inserted at a position in the peptide which is three residues away. The relative positions of the first and second non-natural amino acids in this stapled peptide are designated as (i, i+3). In another embodiment, the first non-natural amino acid at position 3 of SEQ ID NO: 1 or position 4 of SEQ ID NO: 2 can be cross-linked to a second non-natural amino acid located seven residues away (i, i+7) in the peptide. Alternatively, the first non-natural amino acid substitution at position 3 of SEQ ID NO: 1 or position 4 of SEQ ID NO: 2 can be cross-linked to a second non-natural amino acid located four residues away (i, i+4) in the peptide.

A stapled peptide that includes a hydrocarbon staple located near the N-terminus of the peptide can include a first non-natural amino acid inserted before or after position 3 of SEQ ID NO: 1 or position 4 of SEQ ID NO: 2 (before or after the alanine located between the arginine and leucine residues). This first non-natural amino acid can be cross-linked to a second non-natural amino acid that is located three residues away (i, i+3) in the peptide, seven residues away (i, i+7) in the peptide, or four residues away (i, i+4) in the peptide.

Stapled peptides according to the invention can include a non-natural amino acid substitution or insertion located near the C-terminus of the peptide. For example, a stapled peptide according to the invention can include a non-natural amino acid substitution (or insertion before or after) the C-terminal serine residue located at position 22 of SEQ ID NO: 1 or position 23 of SEQ ID NO: 2. This non-natural amino acid can be cross-linked to another non-natural amino acid located three residues away (i, i+3) in the peptide. In other embodiments, the stapled peptide having a first non-natural amino acid substitution at position 3 of SEQ ID NO: 1 or position 4 of SEQ ID NO: 2 can be cross-linked to a second non-natural amino acid located seven residues away (i, i+7) in the peptide or four residues away in the peptide.

In certain embodiments, the stapled peptide according to the invention include a combination of any one of the foregoing hydrocarbon staples located near the N-terminus of the peptide and any one of the foregoing hydrocarbon staples located near the C-terminus of the peptide. For example, the stapled peptides of the invention include the peptides described in Table 1 (bolded residues indicate changes in sequences relative to SEQ ID NO: 1).

TABLE 1

Z-(spacer)-Ser Arg Ala Leu Thr Glu Leu Gln Arg Gln
Arg Leu Glu Pro Phe Arg Gln Arg Leu Trp Asp Ser
Gly-Y
(SEQ ID NO: 1)

Z-(spacer)-Ser Arg Ala Leu Thr Glu Leu Gln Arg Gln
Arg Leu Glu Pro Phe Arg Gln Arg Xaa Trp Asp Ser
Xaa-Y
(SEQ ID NO: 3)

Z-(spacer)-Ser Arg Xaa Leu Thr Glu Xaa Gln Arg Gln
Arg Leu Glu Pro Phe Arg Gln Arg Leu Trp Asp Ser-Y
(SEQ ID NO: 4)

Z-(spacer)-Ser Arg Xaa Leu Thr Glu Xaa Gln Arg Gln
Arg Leu Glu Pro Phe Arg Gln Arg Xaa Trp Asp Ser
Xaa-Y
(SEQ ID NO: 5)

Z-(spacer)-Ser Arg Xaa Leu Thr Glu Xaa Gln Arg Gln
Arg Leu Glu <u>Gly</u> Phe Arg Gln Arg Xaa Trp Asp Ser
Xaa-Y
(SEQ ID NO: 6)

Z-(spacer)-Ser Arg Xaa Leu Thr Glu Xaa Gln Arg Gln
Arg Leu Glu Pro Phe Arg Leu Arg Xaa Trp Asp Ser
Xaa-Y
(SEQ ID NO: 7)

Z-(spacer)-Ser Arg Xaa Leu Thr Glu Xaa Gln Arg Gln
Arg Leu Glu Pro Phe Cys Gln Arg Xaa Trp Asp Ser
Xaa-Y
(SEQ ID NO: 8)

TABLE 1-continued

Z-(spacer)-Ser Arg Xaa Leu Thr Glu Xaa Gln Arg Gln
Arg Leu Glu Pro Phe Cys Leu Arg Xaa Trp Asp Ser
Xaa-Y
(SEQ ID NO: 9)

In Table 1, "Z" is an amino protecting group such as acetyl (Ac), fluorescein thiourea (FITC), biotin (Bt), fluorenylmethoxy-carbonyl (Fmoc) and/or a suitable amino protecting group disclosed in Greene et al., *Protecting Groups in Organic Synthesis*, 3$^{rd}$ ed., (John Wiley & Sons, 1999), the entirety of which is incorporated herein by reference. In table 1, "Y" is a carboxylic acid protecting group such as group that forms an amino-, silyl-, alkyl-, alkenyl-, aryl-, or arylalkyl-protected carboxylic acid. Other suitable carboxylic acid protecting groups are disclosed in Greene et al., *Protecting Groups in Organic Synthesis*, 3$^{rd}$ ed., (John Wiley & Sons, 1999). The "spacer" in Table 1 can be one or more naturally occurring α-amino acids (e.g., A, R, N, C, D, Q, E, G, H, I, L, K, M, F, P, S, T, W, Y, V), non-natural α-amino acids, natural β-amino acids (e.g., β-alanine or N-β-Fmoc-β-alanine), and/or non-natural β-amino acids. In Table 1, "Xaa" is a non-natural amino acid that includes a moiety capable of undergoing a reaction with a second moiety on another non-natural amino acid in the peptide to form a covalent cross-linker between the at least two non-natural amino acids. "Xaa" in Table 1 can refer to the same non-natural amino acids or to different non-natural amino acids within the peptide, provided they are suitable for cross-linking to each other. Thus, each "Xaa" in Table 1 can refer to an α,α-disubstituted cross-linking amino acids; α-methyl, α-alkenyl cross-linking amino acids; and α-hydro, α-alkenyl cross-linking amino acids. Such non-natural cross-linking amino acids are commercially available, e.g., from Sigma-Aldrich or EMD Chemicals. Suitable non-natural cross-linking amino acids suitable for use in a stapled peptide of the invention as well as methods for cross-linking them are described in U.S. Patent Application Publication 2011/0144306 A1, which is specifically incorporated by reference herein in its entirety.

The amino acid sequences of any one of SEQ ID NO: 3-9 can be modified to include one, two, three, or four substitutions, deletions, or insertions. For example, the sequence of SEQ ID NO: 3-8 can be modified at a.a. positions 3, 6, 7, 10, 11, 16, 17, 19, 20, 21, and 23.

The invention also provides methods of treatment and methods related to the treatment of disorders in which LUBAC-mediated cell signaling is dysregulated.

In one aspect, the invention provides a method of killing the activated B-cell like (ABC) subtype of diffuse large B cell lymphoma (DLBCL). DLBCL can be divided into two main molecular subtypes, denoted activated B cell-like (ABC) and germinal center B cell-like (GCB) DLBCL, which differ in their gene expression profiles, oncogenic abnormalities, and clinical behavior (see, e.g., Alizadeh et al., *Nature*, 403: 503-511 (2000); and Shaffer et al., *Annu. Rev. Immunol.*, 30: 565-610 (2012)). In ABC DLBCL, regulatory pathways normally associated with B cell activation are constitutively engaged (Alizadeh et al., supra). In particular, the NF-κB pathway plays an essential role in its pathogenesis by promoting malignant cell survival and inducing expression of the master regulatory transcription factor IRF4 (see, e.g., Davis et al., *J. Exp. Med.*, 194: 1861-1874 (2001); and Yang et al., *Cancer Cell.*, 21: 723-737 (2012)).

Recent genomic and functional studies have elucidated the molecular mechanisms underlying constitutive NF-κB activity in ABC DLBCL, and highlight the central role of the B cell receptor (BCR) and MyD88 signaling pathways. The involvement of BCR signaling in ABC DLBCL was first revealed by the dependence of these lymphomas on the adapter protein CARD11 (see, e.g., Ngo et al., Nature, 441: 106-110 (2006)). In response to BCR signaling, CARD11 forms a multiprotein "CBM" complex with MALT1 and BCL10 and activates IκB kinase (IKK), thereby triggering the classical NF-κB pathway. In 10% of ABC DLBCL tumors, CARD11 sustains oncogenic somatic mutations that constitutively activate IKK and NF-κB (see, e.g., Lenz et al., Science, 319: 1676-1679 (2008)). In other ABC DLBCLs with wild type CARD11, CARD11 is nonetheless essential for survival, demonstrating the dependence of these lymphomas on BCR signaling (a phenomenon called "chronic active" BCR signaling) (see, e.g., Davis et al., Nature, 463: 88-92 (2010)). In more than 20% of ABC DLBCL cases, mutations in the ITAM motifs of the BCR subunits CD79B and CD79A augment chronic active BCR signaling (Davis et al., Nature, 463: 88-92 (2010)), providing genetic evidence that BCR signaling is central to the pathogenesis of ABC DLBCL. A second pathway activating NF-κB in ABC DLBCL is mediated by MYD88, the central adapter in Toll-like receptor signaling (see, e.g., Ngo et al., Nature, 470: 115-119 (2011)). MYD88 silencing is lethal to ABC DLBCL cells due to inhibition of NF-κB and autocrine IL-6/IL-10 signaling through JAK kinase and STAT3 (Ngo et al., Nature, 470: 115-119 (2011); and Lam et al., Blood, 111: 3701-3713 (2008)). In 39% of ABC DLBCL cases, this pathway is activated by somatic, gain-of-function MYD88 mutations. The most common MYD88 mutant, L265P, spontaneously coordinates a signaling complex in which IRAK4 phosphorylates IRAK1, leading to IKK and NF-κB activation (Ngo et al., Nature, 470: 115-119 (2011)).

The invention is based, at least in part, on the discovery that inhibition of LUBAC activity disrupts NF-κB signaling in ABC DLBCL and that LUBAC inhibitors are selectively cytotoxic for ABC DLBCL. Accordingly, the invention provides a method of killing ABC DLBCL that comprises administering a therapeutically effective amount of a LUBAC inhibitor to ABC DLBCL and thereby killing (or inhibiting proliferation) of ABC DLBCL. The LUBAC inhibitor can be one or more peptide inhibitor of the invention (e.g., a peptide comprising any one of SEQ ID NOs: 1-17). The method can include administering a therapeutically effective amount of the LUBAC inhibitor to ABC DLBCL in vitro or in a subject (i.e., in vivo). The LUBAC inhibitor can be administered to ABC DLBCL that is in, for example, a primary cell culture or an animal model of ABC DLBCL.

The invention provides a method of treating a subject that is suffering from ABC DLBCL or at risk for ABC DLBCL. The method includes administering a pharmaceutical composition comprising a therapeutically effective amount of a LUBAC inhibitor to the subject. In certain embodiments, the pharmaceutical composition administered to a subject includes a therapeutically effective amount of one or more peptide inhibitors of the invention (e.g., a peptide comprising the sequence of any one of SEQ ID NOs: 1-17).

As used herein, a subject that is suffering from or at risk for ABC DLBCL can be a subject diagnosed with ABC DLBCL, a subject undergoing treatment for ABC DLBCL, a subject suspected to have ABC DLBCL, or a subject at risk for having ABC DLBCL (for example, a subject at risk for recurrence of ABC DLBCL).

The foregoing method of killing ABC DLBCL and foregoing treatment methods can each further include the co-administration a second therapeutic agent for ABC DLBCL. For example, the method of killing ABC DLBCL or the method of treating ABC DLBCL by administration of a LUBAC inhibitor can further include the co-administration of a cytotoxic, cystostatic, or antiangiogenic agent suitable for use against DLBCL. Such a method can include, for example, the co-administration of rituximab, alemtuzumab, bortezomib, dasatinib, BTK Kinase inhibitors (e.g., PCI-32765), a chemotherapeutic agent, a radiotherapeutic agent, or a combination of the foregoing. The invention provides, for example, methods that include co-administration of a LUBAC inhibitor (e.g., a peptide inhibitor of the invention) and one or more cytotoxic agents used in CHOP, EPOCH, R-CHOP, therapeutic regimens. Such cytotoxic agents include cyclophosphamide, doxorubicin, vincristine, prednisone, etoposide, and derivatives thereof.

Although, the methods of the invention are not bound by or limited to any theory or mechanism of action, there is clinical and experimental evidence indicating that the constitutive activation of NF-κB signaling in ABC DLBCL not only mediates cell survival but also confers resistance to conventional cytotoxic therapy in many cases of ABC DLBCL. In view of LUBAC's role mediating NF-κB activation in ABC disclosed herein, the invention also provides a method of sensitizing ABC DLBCL to cytotoxic agents. The method includes administering a LUBAC inhibitor, e.g., one or more LUBAC peptide inhibitors disclosed herein, to ABC DLBCL and thereby reducing or inactivating resistance to cytotoxic therapy in the ABC DLBCL.

In another aspect, the invention provides a method of treating a disease or pathological condition mediated by LUBAC activity. In one embodiment, the invention provides a method of treating a subject with cancer that is resistant to cytotoxic chemotherapy, radiation therapy, vaccine therapy, or cytokine therapy due to LUBAC activation of NF-κB-signaling. This method of the invention comprises administering to the subject a pharmaceutical composition comprising a therapeutically effective amount of a peptide inhibitor according to the invention (e.g., a peptide inhibitor comprising the sequence of any one of SEQ ID NOs: 1-17). In certain embodiments, the method further includes co-administering a second therapeutic agent which is an agent for cytotoxic chemotherapy, radiation therapy, cytokine therapy, or vaccine therapy.

The invention also provides a method for screening whether a subject suffering from cancer that is resistant to cytotoxic chemotherapy, radiation therapy, or cytokine therapy is a candidate for treatment with a LUBAC inhibitor. The method includes obtaining a sample (biopsy) from the subject that includes cancer cells, then administering to the sample a peptide inhibitor according to the invention (e.g., a peptide inhibitor comprising SEQ ID NOs: 1-17), and co-administering to the sample one or more second therapeutic agents for cytotoxic chemotherapy, radiation therapy, or cytokine therapy. The cancer cells in the sample are assayed for viability before the peptide inhibitor and the second therapeutic agent(s) can exert any cytotoxic effect (e.g., just before administration of the peptide inhibitor and second therapeutic agent(s)). The cells are subsequently assayed for viability at one or more times after the co-administration of the peptide inhibitor and the second therapeutic agent(s) to determine whether there is a significant decrease in the number of viable cancer cells. Such a decrease indicates that the subject is a candidate for treatment with a LUBAC inhibitor.

In some embodiments, the method of screening can further include treating a second control sample from the subject. An equivalent dose or amount of the second therapeutic agent(s), without a peptide inhibitor of the invention, is administered to the control sample. Cancer cells in the sample are assayed for viability before the second therapeutic agent(s) can exert any effect and after administration of the second therapeutic agent(s). If the number of viable cells remaining in the control sample is greater than the number of viable cells in the sample treated by co-administration with a peptide inhibitor and the second therapeutic agent, then the peptide inhibitor has sensitized the cancer cells to the cytotoxic chemotherapy, radiation therapy, or cytokine therapy, and the subject is a candidate for treatment with a LUBAC inhibitor.

In another embodiment, the invention provides a method of treating a condition associated with a dysregulated inflammatory response. LUBAC-signaling has been linked to signaling events which are essential to inflammatory innate immune responses to pathogenic infections. A dysregulated innate inflammatory response is associated with autoimmune disorders, such as, chronic autoinflammation, systemic lupus erythematosus, rheumatoid arthritis, Crohn's inflammatory bowel disease, and psoriasis. Thus, the invention provides a method of treating a subject suffering from a dysregulated inflammatory response, such as, rheumatoid arthritis, chronic autoinflammation, systemic lupus erythematosus, Crohn's inflammatory bowel disease, and psoriasis. The method includes administering to the subject a pharmaceutical composition comprising a therapeutically effective amount of a LUBAC peptide inhibitor according to the invention (e.g., a peptide inhibitor comprising SEQ ID NOs: 1-17).

The terms "treat," "treating," "treatment," and "therapeutically effective" used herein do not necessarily imply 100% or complete treatment. Rather, there are varying degrees of treatment, which one of ordinary skill in the art recognizes as having a potential benefit or therapeutic effect. In this respect, the inventive method can provide any amount of any level of treatment. Furthermore, the treatment provided by the inventive method can include the treatment of one or more conditions or symptoms of the disease being treated.

The terms "co-administering," "co-administration" and "co-administered" used herein refer to the administration of a LUBAC inhibitor (e.g., a peptide inhibitor of the invention) and one or more additional therapeutic agents sufficiently close in time to (i) enhance the effectiveness of the peptide inhibitor or the one or more additional therapeutic agents and/or (ii) reduce an undesirable side effect of the peptide inhibitor or the one or more additional therapeutic agents. In this regard, the LUBAC inhibitor or the peptide inhibitor can be administered first, and the one or more additional therapeutic agents can be administered second, or vice versa. Alternatively, the LUBAC inhibitor (e.g., the peptide inhibitor) and the one or more additional therapeutic agents can be co-administered simultaneously.

The term "subject" is used herein, for example, in connection with therapeutic and screening methods, to refer to human or animal subjects (e.g., mammals). Animal subjects include, but are not limited to, animal models, such as, mammalian models of conditions or disorders associated dysregulated LUBAC-signaling. For example, the subject can be an animal model of ABC DLBCL, or a cancer that is resistant to cytotoxic chemotherapy, radiation therapy, or cytokine therapy. A subject can also be an animal model of an autoimmune disorder associated with dysregulated innate immune response. Alternatively a subject can be a human patient suffering from or at risk for (i) ABC DLBCL, (ii) a cancer that is resistant to cytotoxic chemotherapy, radiation therapy, or cytokine therapy, or (iii) an autoimmune disorder associated with dysregulated innate immune response.

One or more peptide inhibitors of the invention (e.g., peptides comprising SEQ ID NOs: 1-17) can be administered alone or in a composition (e.g., formulated in a pharmaceutically acceptable composition). Such a composition comprises a carrier (e.g., a pharmaceutically acceptable carrier), such as those known in the art. A pharmaceutically acceptable carrier (or excipient) preferably is chemically inert to the peptide inhibitor and has few or no detrimental side effects or toxicity under the conditions of use. The choice of carrier is determined, in part, by the particular method used to administer the composition.

Carrier formulations suitable for parenteral, oral, nasal (and otherwise inhaled), topical, and other administrations can be found in *Remington's Pharmaceutical Sciences* 17$^{th}$ ed., Mack Publishing Co., Easton, Pa. (2000), which is incorporated herein in its entirety by reference thereto. Requirements for effective pharmaceutical carriers in parenteral and injectable compositions are well known to those of ordinary skill in the art. See, e.g., *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986). Accordingly, there is a wide variety of suitable formulations of the composition.

The composition can contain suitable buffering agents, including, for example, acetate buffer, citrate buffer, borate buffer, or a phosphate buffer. The pharmaceutical composition also, optionally, can contain suitable preservatives, such as benzalkonium chloride, chlorobutanol, parabens, and thimerosal.

The composition can be presented in unit dosage form and can be prepared by any suitable method, many of which are well known in the art of pharmacy. Such methods include the step of bringing the peptide inhibitor into association with a carrier that constitutes one or more accessory ingredients. In general, the composition is prepared by uniformly and intimately bringing the peptide inhibitor into association with a liquid carrier, a finely divided solid carrier, or both, and then, if necessary, shaping the product.

The composition can be administered using any suitable method including, but not limited to parenteral, oral, nasal (or otherwise inhaled), and topical administration. Delivery systems useful in the context of the invention include time-released, delayed-release, and sustained-release delivery systems.

A composition suitable for parenteral administration conveniently comprises a sterile aqueous preparation of the peptide inhibitor, which preferably is isotonic with the blood of the recipient. This aqueous preparation can be formulated according to known methods using suitable dispersing or wetting agents and suspending agents.

Sterile powders for sterile injectable solutions can be prepared by vacuum drying and/or freeze-drying to yield a powder of the peptide inhibitor, optionally, in association with a filler or diluent.

A composition suitable for oral administration can be formulated in discrete units such as capsules, cachets, tablets, or lozenges, each containing a predetermined amount of the peptide inhibitor as a powder or granules. A tablet may be made by compression or molding, optionally with one or more accessory ingredients. Compressed tablets may be prepared by compressing in a suitable machine, with the peptide inhibitor being in a free-flowing form, such as a powder or granules, which optionally is mixed with a binder, disintegrant, lubricant, inert diluent, surface peptide inhibitor, or discharging agent. Molded tablets comprised of a mixture of the peptide inhibitor with a suitable carrier may be made by molding in a suitable machine.

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, the proteins of the invention are mixed with solubilizing agents such a Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution, and 1,3-butanediol. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Topical formulations comprise at least one peptide inhibitor dissolved or suspended in one or more media, such as mineral oil, petroleum, polyhydroxy alcohols, or other bases used for topical pharmaceutical formulations. Transdermal formulations may be prepared by incorporating the peptide inhibitor in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

The amount (e.g., therapeutically effective amount) of peptide inhibitor suitable for administration depends on the specific peptide inhibitor used and the particular route of administration. In certain embodiments, for example, peptide inhibitor can be administered in a dose of about 0.5 ng to about 900 ng (e.g., about 1 ng, 25 ng, 50 ng, 100, ng, 200 ng, 300 ng, 400 ng, 500, ng, 600 ng, 700 ng, 800 ng, or any range bounded by any two of the aforementioned values), in a dose of about 1 µg to about 900 µg (e.g., about 1 µg, 2 µg, 5 µg, 10 µg, 15 µg, 20 µg, 25 µg, 30 µg, 40 µg, 50 µg, 60 µg, 70 µg, 80 µg, 90 µg, 100 µg, 200 µg, 300 µg, 400 µg, 500, µg, 600 µg, 700 µg, 800 µg, or any range bounded by any two of the aforementioned values), or in a dose of about 1 mg to about 200 mg (e.g., about 1 mg, 2 mg, 5 mg, 10 mg, 15 mg, 20 mg, 25 mg, 30 mg, 40 mg, 50 mg, 60 mg, 70 mg, 80 mg, 90 mg, 100 mg, 125 mg, 150 mg, 175 mg, or any range bounded by any two of the aforementioned values) per kilogram body weight of the subject. Several doses can be provided over a period of days or weeks.

The invention also provides kits suitable for carrying out the methods of the invention. Typically, a kit comprises two or more components required for performing a therapeutic or screening method of the invention. Kit components include, but are not limited to, one or more peptide inhibitors of the invention, appropriate reagents, and/or equipment. A kit can comprise one or more peptide inhibitors of the invention and a second therapeutic agent, e.g., a cytotoxic, cystostatic, or antiangiogenic agent. Generally, the kit includes peptide inhibitor of the invention suitably packaged, e.g., in a vial, pouch, ampoule, and/or any container appropriate for a therapeutic or screening method. Kit components can be provided as concentrates (including lyophilized compositions), which may be further diluted prior to use, or the kit components can be provided at the concentration intended for use. When peptide inhibitor of the invention is intended to be used in vivo, single dosages may be provided in sterilized containers having the desired amount and concentration of agents.

In another aspect, the invention provides a method for identifying and optimizing LUBAC inhibitors. Generally, the method includes binding a peptide inhibitor of the invention to the RBCK1 UBL domain and evaluating the ability of a test compound to disrupt or inhibit the binding reaction. Peptides of the invention that can be used include, but are not limited to, peptides that include the sequences of SEQ ID NOs 1-16, e.g., RNF 31-N, RNF 31-NC, RNF 31-NC, RNF31-NC P2G, and RNF31-NC Q2L described herein. The UBL domain can be provided in context of the entire RBCK protein or as a fragment thereof that includes the portion of the UBL that binds to the LUBAC inhibitor of the invention.

In one embodiment, the method can include tagging the peptide inhibitor of the invention (or tagging the UBL domain) to a fluorescent moiety. The peptide or the UBL domain can be fixed (e.g., immobilized or covalently bound) to a substrate and contacted to its fluorescently tagged partner to thereby create a substrate-bound dimer. The amount of fluorescently tagged peptide or UBL domain that binds to substrate can be determined, e.g., by detecting the strength of signal from the fluorescent moiety that is bound to the substrate. A fluorescence binding curve can be generated. A test compound can be added to the reaction and the ability of the test compound to disrupt or inhibit the fluorescently tagged peptide or UBL domain from forming a substrate-bound dimer can be measured, for example, by detecting a reduction in the signal produced by the fluorescent moiety that is bound to the substrate. A test compound that significantly reduces the fluorescence signal is a candidate peptide inhibitor or a candidate optimized peptide inhibitor of LUBAC.

Variations of the foregoing method can be performed. For example, a fluorescent moiety can be attached to either the peptide of the invention or the UBL domain, and a quencher moiety can be attached to the other. After allowing the peptide of the invention to bind to the UBL domain, a baseline signal of the fluorescent moiety is measured. A test compound can be added and the ability of the test compound to disrupt or inhibit the binding reaction of the peptide inhibitor and the UBL domain can be measured, for example, by detecting an increase in the signal produced by the fluorescent moiety. A test compound that significantly increases the fluorescence signal in this assay is a candidate peptide inhibitor or a candidate optimized peptide inhibitor of LUBAC. Other techniques for detecting the ability of test compounds to disrupt protein binding can be used. These include, for example, surface plasmon resonance (SPR) binding assays, co-immunoprecipitation, affinity chromatography, and the like.

As used herein a test compound can be a small molecule compound. Alternatively, the test compound can be a peptide of the invention which includes the amino acid sequences of any one of SEQ ID NOs: 3-16, which has been modified to include one, two, three, or four substitutions, deletions, or insertions. For example, the test compound can include the sequence of any one SEQ ID NOs: 3-16 can be modified at a.a. positions 3, 6, 7, 10, 11, 16, 17, 19, 20, 21, and 23.

The following examples further illustrate the invention but, of course, should not be construed as in any way limiting its scope.

Example 1

This example demonstrates the discovery of LUBAC mutations in ABC DLBCL patients.

A screen for mutations using RNA-seq data from 56 ABC DLBCL biopsies identified two recurrent missense mutations in LUBAC RNF31 component that change glutamine 584 to histidine (Q584H; n=2) and glutamine 622 to leucine (Q622L; n=3). Both of these mutations were identified as rare single-nucleotide polymorphisms (SNPs) among healthy individuals in the 1000 Genomes Project (Abecasis et al., Nature, 491: 56-65 (2012)) and GO Exome Sequencing Project (Tennessen et al., Science, 337: 64-9 (2012)). In healthy individuals, Q584H (SNP accession rs184184005) had a minor allele frequency (MAF) of 0.19% and 0.098%, respectively, whereas Q622L (SNP accession rs149481717) had a MAF of 0.24% and 0.409%, respectively. Both SNPs are located in a region of the RNF31 gene that encodes the ubiquitin-associated (UBA) domain, which interacts with the ubiquitin-like (UBL) domain of RBCK1, leading to LUBAC enzyme formation.

The portion of RNF31 that includes these SNPs was sequenced in 561 biopsy samples of various lymphoma subtypes. In 103 ABC DLBCL biopsies, the Q584H was found in 2 cases and Q622L in 6 cases, with an overall frequency of 7.8%. This frequency is 12-fold or 27-fold higher than in the GO Exome Sequencing Project12 and 1000 Genomes Project11 cohorts. Among 458 samples of other lymphoid malignancies, 3 Q622L cases were identified, one each in GCB DLBCL, follicular lymphoma, and Hodgkin lymphoma. No cases had Q584H. Thus, the frequency of both SNPs in non-ABC DLBCL cases of was 0.655% (3/458), which is similar to the frequency in the healthy cohorts (p=0.4136), but 12-fold lower than the frequency in ABC DLBCL (p=0.00016). In the one ABC DLBCL case with available germ line DNA, RNF31 Q584H was confirmed to be a germline variant.

The foregoing results show that mutations in LUBAC RNF31 are associated with ABC DLBCL and that mutations can be diagnostic of ABC DLBCL.

Example 2

This example demonstrates the biological consequences of reducing LUBAC activity in ABC DLBCL and GCB DLBCL and its consequences on cell viability.

Small hairpin RNAs (shRNAs) were developed to knock down the expression of the HOIP ("RNF31") and SHARPIN subunits of LUBAC. The shRNA targeting sequence for RNF31 was GAAGACAAGGTTGAAGATGAT (SEQ ID NO:18); shRNA targeting sequence for SHARPIN was GAGCGCAGCCTTGCCTCTTAC (SEQ ID NO:19). The shRNAs were placed under control of an inducible promoter in a pMSCV-based retroviral vector (pRSMX_Puro) with two expression cassettes. The first cassette drives constitutive expression of a selectable marker (puromycin resistance) fused with GFP, and the other cassette drives placed shRNA expression under control of the bacterial tetracycline repressor. The vector and expression system were described in Lenz et al., Proc. Natl. Acad. Sci. USA 105: 13520-13525 (2008) and Shaffer et al., Nature, 454L: 226-231 (2008).

Each shRNA vector construct was transduced into ABC DLBCL and GCB DLBCL cell lines in conjunction with mutant ecotropic envelope-expressing plasmid pHIT/EA6× 3*, and gag-pol expressing plasmid pHIT60 was used to transfect the 293T cells using the LIPOFECTAMINE 2000 reagent (Invitrogen, Carlsbad, Calif.) as described previously in Ngo et al., Nature, 441: 106-110 (2006). ABC cell lines included HBL1, TMD8, OCI-Ly3, OCI-Ly10, U2932, and DCLBL2 and GCB cell lines included OCI-Ly19, OCI-Ly8, SUDHL4, and BJAB. All cell lines are from American Type Culture Collection (ATCC) (Manassas, Va.). All cell lines had previously been modified to express an ecotropic retroviral receptor and a fusion protein of the Tet repressor and the blasticidin resistance gene (Ngo et al. (2006)). Cell lines were grown in media to log phase at 37° C., 5% $CO_2$ as follows: GCB-derived cells were grown in RPMI-1640 (Invitrogen) +10% FBS Defined (Hyclone, Logan Utah)+penicillin streptomycin mixture ("Pen/Strep") (Invitrogen), and ABC-DLBCL-HBL1, TMD8, U2932, HLY1, OCI-Ly3, OCI-Ly10, SUDHL2, and DLBCL2 were grown in RPMI (Invitrogen) +20% human serum+Pen/Strep (Invitrogen). Transfected cells that were positive for green fluorescent protein expression (GFP+) were selected.

The toxicity of individual shRNA sequences was tested using fluorescence-activated cell sorting (FACS) to determine the fraction of live cells that were GFP-positive two days after transduction. Expression of shRNA was induced with doxycyline (20 ng/mL) at time 0, and the fraction of GFP-positive live cells was determined at various intervals following induction. Parallel cultures were prepared with a vector expressing a control shRNA. The GFP-positive fraction from the test shRNA cultures was normalized to the GFP-positive fraction on day 0. FIG. 1 indicates the percent fraction of GFP+, shRNA-expressing cells at the indicated times (days) following induction relative to the initial number of such cells at time 0.

The cell viability assay results in FIG. 1 show that inducing expression of shRNA against RNF31 was toxic to most ABC DLBCL lines. The results in FIG. 1 also indicate that depletion of RNF31 had little effect on the GCB DLBCL lines tested. Similar results were obtained when shRNAs against SHARPIN were induced in ABC and GCB cell lines.

The foregoing results indicate that LUBAC plays an oncogenic role and maintains viability in ABC DLBCL cells. The results also indicate that depletion of LUBAC activity, in accordance with the invention, is selectively toxic for ABC DLBCL.

Example 3

This example demonstrates the biological consequences of reducing LUBAC activity in ABC DLBCL, including its effect on the constitutive NF-κB activation in ABC DLBCL.

In a first experiment, stable ABC DLBCL cell lines were generated for the inducible expression of shRNAs to knock down RNF31 or SC4 (negative control). HBL1 cells were transfected with the same constructs used in Example 2. Inducible expression of shRNAs was confirmed by immunoblot analysis of whole cell lysates probed with antibodies to IKKβ kinase and phosphorylated IKKβ kinase ("p-IKKβ"), IκBα and phosphorylated IκBα, RNF31, and actin. Anti-IKKβ and anti-phospho-IKKβ antibodies were obtained from Cell Signaling Technologies (Boston, Mass.), and anti-β-actin antibody was obtained from Sigma (St. Louis, Mo.). Western blotting was done by lysing cell pellets in modified RIPA buffer (50 mM Tris-HCl pH 7.5, 150 mM NaCl, 1% NP40, 0.25% deoxycholic acid, 1 mM EDTA) supplemented with a protease cocktail inhibitor tablet and a phosphatase cocktail inhibitor tablet (Roche, Indianapolis, Ind.), 1 mM DTT, 1 mM Na$_3$ VaO$_4$, 1 mM PMSF. Protein concentration was measured by BCA Protein Assay Kit (Thermo Scientific). Total proteins were separated on 4% to 12% SDS-polyacrylamide gels and transferred to nitrocellulose membranes for blotting with antibodies. The immunoblots depicted in FIG. 2A confirm the shRNA-mediated depletion of RNF31 in experimental cell lines #3 and #10 (as compared to control cell line expressing SC4 shRNA). The immunoblots also confirm that inactivation of RNF31 inhibited NF-κB activity, as measured by the reduction of phosphorylated IκB kinase β and phosphorylated IκBα.

In a second experiment, HBL1 and TMD8 ABC DLBCL lines were engineered to contain an NF-κB-driven luciferase reporter. Vectors expressing an IκBα-luciferase fusion protein were constructed using Photinus luciferase from pGL3 vector (Promega, Madison, Wis.) as the reporter and *Renilla* luciferase construct from phRL-TK (Promega) was used for normalization. Stable clones were identified that were responsive to IκBα-small-molecule inhibitor (see Lam et al, *Clin Cancer Res,* 11: 28-40 (2005)). After development with the DUAL-GLO luciferase assay system (Promega), the ratio of IκBα-Photinus to *Renilla* luminescence was normalized to that in untreated or uninduced cultures. The IκBα assay, which relies on the correlation between NF-κB activity and IKKβ kinase activity, was previously described in Lenz et al, *Science,* 319: 1676-1679 (2008). In brief, IKKβ kinase phosphorylates IκBα, which leads to degradation of IκBα (an inhibitor of NF-κB) and thereby activates NF-κB.

The engineered cells were transfected with control (SC4) or RNF31 shRNAs under the control of a doxycyline promoter as described in Example 2. Expression of shRNA was induced with doxycyline, and relative amounts of NF-κB Luciferase reporter activity was measured and normalized relative to control (SC4) shRNA. As additional controls, the expression of NF-κB Luciferase reporter activity was measured in cells that were not expressing shRNAs and which were either treated with the specific IKKβ inhibitor ("MLM-120B") or untreated ("No Rx"). Experiments were done in triplicate and the results are shown in FIG. 2B (error bars indicate standard error of the mean (SEM)). The results in FIG. 2B show that shRNA-mediated depletion of RNF31 caused a rise in the IκBα-luciferase reporter, which is indicative of IKKβ inhibition and decreased NF-κB activity.

A third experiment was done using a different reporter system for NF-κB activity. HBL1 and TMD8 ABC DLBCL lines cell lines were created with an NF-κB transcriptional reporter by transduction with lentiviral particles containing an inducible NF-κB-responsive luciferase reporter construct (SA Biosciences, Valencia, Calif.) and selected with puromycin. Luciferase activity was measured using the DUAL-LUCIFERASE™ Reporter Assay System (Promega) on a Microtiter Plate Luminometer (Dyn-Ex Technologies, Chantilly, Va.). The transduced HBL and TMD8 cell lines were then transfected with constructs that inducibly express control (SC4) or RNF31 shRNAs described above. Expression of shRNAs was induced using doxycyline, and the luciferase reporter activity in shRNF31 expression cells was measured and normalized relative to control (SC4). Cells were also treated with the specific IKKβ inhibitor (MLN120B) as a positive control. Experiments were done in triplicate, and results are shown in FIG. 2C (error bars indicate SEM). The results in FIG. 2C show that depletion of RNF31 decreased activity of the NF-κB-driven luciferase reporter, which indicates that depletion of RNF31 leads to IKKβ inhibition and decreased NF-κB activity.

A fourth experiment was done to determine the effect of reducing LUBAC activity on NF-κB translocation to the nucleus. Nuclear fractions were prepared from the HBL1 ABC DLBCL cell lines selected for expression of control (SC4) or RNF31 shRNAs, as described above. Nuclear p65 DNA-binding activity was determined by ELISA. Nuclear p65 (RELA) is a component of NF-κB heterodimers in ABC DLBCL. NF-kB p65 DNA-binding activity was measured using ELISA kits obtained from TransAM (Carlsbad, Calif.) according to the manufacturer's instructions. Experiments were done in triplicate and ELISA results are shown in FIG. 2D, left panel (error bars show SEM). Cytosolic cell fractions were blotted for antibodies against RNF31 and actin (as described above) to demonstrate the specificity of the cellular fraction. The ELISA assay results in FIG. 2D, left panel, indicate that depletion of RNF31 decreased the nuclear DNA binding activity of the NF-κB p65 subunit.

Together, these results indicate the significant role of LUBAC in maintaining constitutive NF-κB activation and viability in ABC DLBCL.

Example 4

This example demonstrates that LUBAC contributes to BCR signaling in ABC DLBCL cells.

The role of LUBAC in the BCR and MyD88 pathways, which govern NF-κB activity in ABC DLBCL, was investigated using co-immunoprecipitation experiments. ABC DLBCL and GCB DLBCL cells were lysed in an endogenous lysis buffer (20 mM Tris-HCl pH 7.6, 150 mM NaCl, 1 mM EDTA, 1% Triton X-100, 30 mM NaF, and 2 mM sodium pyrophosphate) supplemented with complete protease inhibitor cocktail (Roche, Basel, Switzerland), phosphatase inhibitor tablet (Roche, Basel, Switzerland), 1 mM DTT, 1 mM Na$_3$VaO4, and 1 mM PMSF. Cleared lysates were incubated overnight with polyclonal anti-MALT, anti-IRAK1, and control antibodies. Immunoprecipitates were washed five times with 0.5M NaCl lysis buffer, separated by SDS-PAGE, transferred to nitrocellulose and analyzed by immunoblotting.

RNF31 was shown to associate with MALT1 and, to a lesser extent, IRAK1 in ABC DLBCL lines, suggesting that the LUBAC complex could play a role in both pathways Using an antibody specific for linear ubiquitin (Tokunaga et al., *Nat. Cell. Biol.,* 11: 123-132 (2009); and Tokunaga et al., *Nature,* 471: 633-636 (2011)), this modification was detectable on IKKγ/NEMO immunoprecipitated from ABC DLBCL cells, as expected, but also on IRAK1. Neither protein was modified by linear ubiquitin in the control GCB DLBCL line. In contrast, linear ubiquitin was not detectable in immunoprecipitates of MALT1 or CARD11. Chronic active BCR signaling in ABC DLBCL causes MALT1 to proteolytically cleave A20, a negative regulator of NF-κB signaling (Hailfinter et al., *Proc. Natl. Acad. Sci. USA*, 106: 19946-19951 (2009); Ferch et al., *J. Exp. Med.*, 206: 2313-2320 (2009)). Knockdown of RNF31 decreased A20 proteolysis in ABC DLBCL lines, implicating LUBAC in this regulatory process. Acute BCR cross-linking by anti-IgM antibodies in a GCB DLBCL line (BJAB) or in an ABC DLBCL line (HBL1) rapidly increased IKKβ phosphorylation, but knockdown of RNF31 compromised this induction, reinforcing the view that LUBAC plays a key role in NF-κB activation during BCR signaling. ABC DLBCL lines depleted of RNF31 were sensitized to the BTK kinase inhibitor ibrutinib, which blocks chronic active BCR signaling in ABC DLBCL (Davis et al., *Nature*, 463: 88-92 (2010)), and to lenalidomide, which reduces CARD11 levels by inhibiting IRF4 (Yang et al., *Cancer Cell*, 21: 723-737 (2012)).

The results of this example demonstrate that LUBAC is associated with the CBM complex and contributes to BCR signaling in ABC DLBCL cells.

Example 5

This example demonstrates that RNF31 SNPs promote NF-κB activity in ABC DLBCL cells.

A small region of the RNF31 UBA domain, from amino acids 579 to 623, binds to the UBL domain of RBCK1 (Yagi et al., *EMBO Reports*, 13: 462-468 (2012)). The RNF31 Q584H and Q622L mutants reside in this region, suggesting that they might promote LUBAC complex formation and subsequent NF-κB activation. When these RNF31 mutants or wild type RNF31 were expressed in ABC DLBCL cells at equivalent levels, Q622L and Q584H increased the activity of an NF-κB-driven luciferase reporter more effectively than wild-type RNF31. Expression levels of two well-known NF-κB target genes, NFKBIA and IRF4, were elevated by the RNF31 mutants more than by wild type RNF31. The RNF31 mutants were also more active in stimulating IKK activity than wild type RNF31, as measured by an IκB kinase activity reporter assay (see, e.g., Lenz et al., *Science*, 319: 1676-1679 (2008)). The RNF31 mutants also were superior in stimulating phosphorylation of IKK and its substrate IκBα, and in inducing nuclear NF-κB p65 DNA binding activity. When expressed in GCB DLBCL BJAB cells, the RNF31 mutants induced expression of the NF-κB target gene CD83, especially in response to anti-IgM-induced BCR activation, which supports the hypothesis that LUBAC contributes to BCR-induced engagement of NF-κB. In addition, RNF31 mutants were more effective than wild type RNF31 in stimulating MALT1-dependent cleavage of A20 in ABC DLBCL cells. While both mutant and wild type RNF31 isoforms interacted with MALT1 equivalently, A20 was more effectively recruited to the CBM complex in ABC DLBCL cells expressing mutant RNF31 than in cells expressing wild type RNF31.

The results of this example demonstrate that RNF31 mutants may promote A20 cleavage by stimulating LUBAC ubiquitination activity and increasing A20 recruitment to the CBM complex.

Example 6

This example demonstrates that γ subunit of IKK (IKKγ/NEMO) is a physiological substrate of LUBAC in ABC DLBCL.

An experiment was done to determine whether or not LUBAC is involved in the ubiquitination of IKK (NEMO/IKKγ) in ABC DLBCL. In other cell types, NEMO is a substrate of a LUBAC E3 complex, and linear ubiquitination of NEMO is required for IKK activity. Haas et al., *Mol. Cell*, 36: 831-844 (2009); Tokunaga et al., *Nature Cell Biol.*, 11: 123-132 (2009).

HBL1 ABC DLBCL was transfected with vectors expressing control (SC4) or RNF31 shRNAs, as described above. For ubiquitination assays, transfected and untransfected cells were boiled 10 minutes in 1% SDS before immunoprecipitation. Boiled lysates were diluted to 0.1% SDS with a modified RIPA buffer (50 mM Tris-HCl pH 7.5, 150 mM NaCl, 1% NP40, 0.25% deoxycholic acid, 1 mM EDTA, supplemented with protease inhibitors and 5 mM N-ethylmaleimide (Sigma). Cleared lysates were incubated overnight with polyclonal anti-NEMO/IKKγ antibody FL-419 (Santa Cruz Biotechnology, Dallas, Tex.). Immunoprecipitated material was immunoblotted with polyclonal antibody for ubiquitin (P4D1 from Santa Cruz Biotechnology) and monoclonal antibody for NEMO/IKKγ (BD-Pharmingen, San Diego, Calif.). Resulting immunoblots for ubiquitin and NEMO are shown in FIG. 3, two upper panels. Total cell lysates were separately immunoblotted with antibodies (described above) for RNF31, NEMO, and actin as shown in FIG. 3, three lower panels.

The immunoblots of immunprecipitated material ("IP: NEMO") indicate the presence of a stable polyubiquitinated form of NEMO in ABC DLBCL (see "sh Control" and "Untransfected" lanes in FIG. 3, upper panel). The immunoblots also indicate that depletion of RNF31 impaired NEMO polyubiquitination (see "shRNF31 #3" and "shRNF31 #10" lanes in FIG. 3, upper panel).

These results indicate that NEMO ubiquitination is dependent on LUBAC activity in ABC DLBCL cells.

Example 7

This example demonstrates LUBAC peptide inhibitors in accordance with the invention.

Stapled peptides inhibitors based on the α-helix spanning amino acids 606-628 (Ser Arg Ala Leu Thr Glu Leu Gln Arg Gln Arg Leu Glu Pro Phe Arg Gln Arg Leu Trp Asp Ser Gly (SEQ ID NO: 1)) of RNF31 were synthesized and examined for their ability to inhibit NF-κB activation in ABC DLBCL cells. The three dimensional structure of the RNF31 UBA α-helix domain interacting with RBCK1 UBL domain was obtained from the Research Collaboratory for Structural Bioinformatics Protein Data Bank. PDB ID 4DBG; Yagi et al., *EMBO Reports*, 13: 462-468 (2012). Peptide synthesis, olefin metathesis, FITC derivatization, reverse-phase HPLC purification, and amino acid analysis was done as previously reported Bernal et al, *J. American Chem. Soc.*, 129: 2456-2457 (2007).

The peptide inhibitors are modified at their amino terminus by inclusion of an acetate cap and the non-amino spacer β-alanine. The amino terminus-modified peptide with wild type amino acids 606-627 of sequence of RNF31 is referred to as "RNF31-wt" (SEQ ID NO: 2). Further modified versions of this peptide include additional substitutions and insertions of α,α-disubstituted non-natural amino acids containing olefin-bearing tethers as described in Walensky et al., *Science*, 305: 1466-1470 (2004). Specifically, the cross-linking, non-natural amino acid (S)-pentenylalanine was substituted or inserted at each position indicated "Xaa" in the sequences of Table 2 below. Prior to releasing peptides from synthetic resin solid phase, ruthenium-mediated olefin metathesis reaction was performed to cross-link each non-natural amino acid to the identical amino acid located four residues away (i, i+4) and thereby create hydrocarbon "staples" at the C-terminus of the alpha-helix in "RNF31-C" (SEQ ID NO: 10), at the N-terminus of the alpha-helix in "RNF31-N" (SEQ ID NO: 11), and at both N- and C-terminus of "RNF31-NC" (SEQ ID NO: 12) shown in Table 2, below.

TABLE 2

| Peptide Name | Sequence |
|---|---|
| RNF31-wt | Ac-βAla Ser Arg Ala Leu Thr Glu Leu Gln Arg Gln Arg Leu Glu Pro Phe Arg Gln Arg Leu Trp Asp Ser-NH₂ (SEQ ID NO: 2) |
| RNF31-C | Ac-βAla Ser Arg Ala Leu Thr Glu Leu Gln Arg Gln Arg Leu Glu Pro Phe Arg Gln Arg Xaa Trp Asp Ser Xaa-NH₂ (SEQ ID NO: 10) |
| RNF31-N | Ac-βAla Ser Arg Xaa Leu Thr Glu Xaa Gln Arg Gln Arg Leu Glu Pro Phe Arg Gln Arg Leu Trp Asp Ser-NH₂ (SEQ ID NO: 11) |
| RNF31-NC | Ac-βAla Ser Arg Xaa Leu Thr Glu Xaa Gln Arg Gln Arg Leu Glu Pro Phe Arg Gln Arg Xaa Trp Asp Ser Xaa-NH₂ (SEQ ID NO: 12) |

The ability of these peptides to inhibit NF-κB activity in ABC DLBCL was determined using the NF-κB luciferase reporter assay described above. HBL1 ABC DLBCL cell line was transfected with the wild-type RNF31-wt peptide or the stapled RNF31 peptides shown in Table 2. Negative control cells were treated with dimethyl sulfoxide (DMSO), and positive control cells were treated with Bruton's tyrosine kinase (Btk) inhibitor ibrutinib. Ibrutinib has been reported to reduce NF-κB activity in ABC cells. Cells were treated with peptides at concentrations of 5 μM or 20 μM for 2 days. Relative NF-κB-luciferase reporter activity was normalized and measured relative to control (DMSO-treated) cells. The results of triplicate experiments are shown in FIG. 4 (error bars indicate the SEM). The NF-κB-luciferase reporter activity shown in FIG. 4 indicates that the RNF31-N (SEQ ID NO: 11) and RNF31-NC (SEQ ID NO: 12) peptides, which contain internal cross-links within their amino-terminal regions, strongly inhibit NF-κB in ABC DLBCL cells. The results also indicate that RNF31-C (SEQ ID NO: 10) peptide and the RNF31-wt (SEQ ID NO: 2) peptide had less of an effect.

The ability of RNF31 stapled peptides to disrupt LUBAC complex formation was tested by co-transfecting HEK-293 cells for 24 hours with constructs expressing two fusion proteins: an influenza hemagglutinin (HA)-RBCK1 fusion and c-Myc protein (Myc)-RNF31. The tagged protein fusions vectors have been described in Kirisako, et al, *EMBO J.*, 25: 4877-4887 (2006). RNF31 point mutants were obtained with QUICKCHANGE™ site directed mutagenesis kit from Stratagene (Santa Clara, Calif.) and verified by dye termination sequencing. Co-transfected cells were then treated with DMSO (control) or with the RNF31-wt and stapled RNF31 peptides in Table 2 at concentrations of 5 μM or 20 μM for an additional 24 hours. Cells were immunoprecipitated with anti-HA antibody and the immunoprecipitated material was immunoblotted using anti-Myc and anti-HA antibodies as shown in FIG. 5, upper immunoblot panels. Anti-Myc antibody was obtained from Abcam (Cambridge, Mass.), and anti-HA was obtained from Miltenyi Biotec (Auburn, Calif.). Total cell lysates were also immunoblotted using these antibodies and anti-actin, as shown in FIG. 5, lower immunoblot panels. Immunoblots were analyzed by densitometry and the abundance of RBCK1 and RNF31 interaction was determined relative to DMSO control. The relative abundance of LUBAC subunit interactions are shown in FIG. 6. The amino-terminal cross-linked peptides RNF31-N (SEQ ID NO: 11) and RNF31-NC (SEQ ID NO: 12) inhibited RBCK1/RNF31 interaction in a dose-dependent fashion, whereas RNF31-C (SEQ ID NO: 10) peptide and the RNF31-wt (SEQ ID NO: 2) peptide had little if any effect.

These results indicate that stapled peptides according to the invention are cell permeable and interfere with LUBAC function. The results also indicate that peptide inhibitors according to the invention decrease NF-κB activity in ABC DLBCL by disrupting LUBAC complex formation.

Example 8

This example demonstrates that LUBAC peptide inhibitors according to the invention are cytotoxic to ABC DLBCL.

ABC and GCB DLBCL cell lines were treated with RNF31 stapled peptides of Table 2 at concentrations of 5 μM or 20 μM for four days. Cell viability was determined using the following MTS assay. Cells were plated in triplicate at a density of 15,000 cells per well in 96-well plates. Cell viability after indicated treatments was assayed by adding 3-(4,5-dimethylthiazol-2-yl)-5-(3-carboxymethoxyphenyl)-2-(4-sulphophenyl)-2H tetrazolium and an electron coupling reagent (phenazine methosulphate from Promega, Madison, Wis.), incubated for 3 hours and measured by the amount of 490 nm absorbance using a 96-well plate reader. The background was subtracted using a media only control. The results of these MTS assays done in triplicate are shown in FIGS. 7A-7D (error bars indicate the SEM), and cell viability is expressed as the fraction of cells remaining after four days treatment, relative to the initial number of cells at the start of treatment (time 0). The results of MTS cell viability assay indicate that amino-terminal cross-linked peptides RNF31-N (SEQ ID NO: 11) and RNF31-NC (SEQ ID NO: 12) were toxic to ABC DLBCL cell lines but had little effect on GCB DLBCL cell lines tested.

These results further support the findings in Example 2 and FIG. 1 which show that GCB DLBCL cells do not depend on LUBAC for survival. Thus, these results further indicate that LUBAC peptide inhibitors according to the invention are selectively toxic to ABC DLBCL.

Example 9

This example demonstrates additional LUBAC peptide inhibitors in accordance with the invention.

The stably cross-linked ("stapled") peptides listed in Table 3 are synthesized as described in Example 7.

TABLE 3

| Peptide Name | Sequence |
|---|---|
| RNF31-NC P2G | Ac-βAla Ser Arg Xaa Leu Thr Glu Xaa Gln Arg Gln Arg Leu Glu <u>Gly</u> Phe Arg Gln Arg Xaa Trp Asp Ser Xaa-NH₂ (SEQ ID NO: 13) |
| RNF31-NC Q2L | Ac-βAla Ser Arg Xaa Leu Thr Glu Xaa Gln Arg Gln Arg Leu Glu Pro Phe Arg <u>Leu</u> Arg Xaa Trp Asp Ser Xaa-NH₂ (SEQ ID NO: 14) |

TABLE 3-continued

Peptide Name | Sequence
---|---
RNF31-NC R2C | Ac-βAla Ser Arg Xaa Leu Thr Glu Xaa Gln Arg Gln Arg Leu Glu Pro Phe <u>Cys</u> Gln Arg Xaa Trp Asp Ser Xaa-NH₂ (SEQ ID NO: 15)
RNF31-NC R2CL | Ac-βAla Ser Arg Xaa Leu Thr Glu Xaa Gln Arg Gln Arg Leu Glu Pro Phe <u>Cys Leu</u> Arg Xaa Trp Asp Ser Xaa-NH₂ (SEQ ID NO: 16)
RNF31-Neg | Ac-βAla Ser Arg Xaa Leu Thr Glu Xaa Ala Arg Gln Arg Ala Glu Pro Ala Arg Gln Arg Xaa Trp Asp Ser Xaa-NH₂ (SEQ ID NO: 17)

The stably cross-linked ("stapled") peptides listed in Table 3 are tested as described in Example 7, and the tests results indicate that peptides RNF31-NC P2G (SEQ ID NO: 13), RNF31-NC Q2L (SEQ ID NO: 14), RNF31-NC R2C (SEQ ID NO: 15), and RNF31-NC R2CL (SEQ ID NO: 16) are peptide inhibitors according to the invention that interfere with LUBAC function and are selectively cytotoxic to ABC DLBCL.

Example 10

This example demonstrates the inhibitory effect of LUBAC peptide inhibitors RNF31-NC Q2L and RNF31-wt in accordance with the invention.

The unstapled peptide of SEQ ID NO:1, when added to ABC DLBCL cells directly, had little or no effect in the NF-κB assay, the IκBα assay, and the cell viability (MTS) assay described above. In contrast, stapled wild type (RNF31-wt) and Q622L (RNF31-NC Q2L) peptides inhibited NF-κB activity (FIG. 8A), decreased IκBα activity (FIG. 8B), and decreased cell viability (FIG. 8C). In each of these assays, the stapled Q622L peptide had the greatest activity, in keeping other experiments that suggested that RNF31 Q622L has increased affinity for RBCK1.

These results indicate that LUBAC inhibitors are effectively cytotoxic against ABC DLBCL and could potentially be used as inhibitors of autoimmune or inflammatory disorders.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A cell permeable peptide comprising:
   (i) any one of SEQ ID NOs: 2-16, or
   (ii) SEQ ID NO: 20 having 45 amino acids or fewer in length;
   wherein when additional amino acids are present in addition to those in the sequence of the SEQ ID NO, those additional amino acids are between the amino protecting group and the sequence of the SEQ ID NO, between the carboxylic acid protecting group and the sequence of the SEQ ID NO, or between the amino protecting group and between the carboxylic acid protecting group and the sequence of the SEQ ID NO.

2. The cell permeable peptide of claim 1, wherein the peptide includes a linker group, or one or more non-proteogenic amino acids, or a combination thereof.

3. The cell permeable peptide of claim 1, wherein the peptide comprises any one of SEQ ID NOs: 2-9.

4. The cell permeable peptide of claim 1, wherein the peptide comprises any one of SEQ ID NOs: 11-16.

5. The cell permeable peptide of claim 1, wherein the peptide comprises any one of SEQ ID NOs: 2-16 and wherein the peptide comprises 45 amino acids or fewer in length.

6. The cell permeable peptide of claim 1, wherein the peptide comprises the sequence of SEQ ID NO: 4.

7. The cell permeable peptide of claim 6, wherein each non-natural amino acid is (S)-pentenylalanine.

8. The cell permeable peptide of claim 1, wherein there are no additional amino acids in the sequence.

9. The cell permeable peptide of claim 8, wherein the peptide consists of the sequence of SEQ ID NO: 4.

10. The cell permeable peptide of claim 9, wherein each non-natural amino acid is (S)-pentenylalanine.

11. A cell permeable peptide consisting of any one of SEQ ID NOs: 2-16 and 20.

12. A method of treating activated B-cell like diffuse large B cell lymphoma (ABC DLBCL) in a subject, which method comprises administering to the subject a composition comprising an effective amount of the peptide of claim 1.

13. The method of claim 12, wherein the peptide includes a linker group, or one or more non-proteogenic amino acid insertions or substitutions, or a combination thereof.

14. The method of claim 12, wherein the peptide comprises a sequence selected from the group consisting of SEQ ID NOs: 2-9.

15. The method of claim 12, wherein the peptide comprises a sequence selected from the group consisting of SEQ ID NOs: 11-16.

16. The method of claim 12, further comprising administering chemotherapy to the subject.

17. The method of claim 12, further comprising administering radiation to the subject.

18. The method of claim 12, wherein the peptide comprises any one of SEQ ID NOs: 2-16 and wherein the peptide comprises 45 amino acids or fewer in length.

19. A method of killing ABC DLBCL, wherein the method comprises administering to ABC DLBCL a composition comprising the peptide of claim 1.

20. The method of claim 19, wherein the peptide includes, a linker group, one or more non-proteogenic amino acids, or a combination thereof.

21. The method of claim 19, wherein the peptide comprises a sequence selected from the group consisting of SEQ ID NOs: 2-9.

22. The method of claim 19, wherein the peptide comprises a sequence selected from the group consisting of SEQ ID NOs: 11-16.

23. The method of claim 19, wherein the method further comprising administering chemotherapy or radiation to the cell.

24. The method of claim 19, wherein the LUBAC inhibitor is a peptide inhibitor comprising any one of SEQ ID NOs: 2-16 and wherein the peptide comprises 45 amino acids or fewer in length.

25. A method of treating rheumatoid arthritis in a subject, which method comprises administering to the subject a composition comprising an effective amount of the peptide of claim 1.

26. The method of claim 25, wherein the peptide includes, a linker group, or one or more non-proteogenic amino acid insertions or substitutions, or a combination thereof.

27. The method of claim 25, wherein the peptide comprises a sequence selected from the group consisting of SEQ ID NOs: 2-9.

28. The method of claim 25, wherein the peptide comprises a sequence selected from the group consisting of SEQ ID NOs: 11-16.

29. The method of claim 25, wherein the LUBAC inhibitor is a peptide inhibitor comprising any one of SEQ ID NOs: 2-16 and wherein the peptide comprises 45 amino acids or fewer in length.

30. A method of treating cancer that is resistant to cytotoxic chemotherapy, radiation therapy, vaccine therapy, or cytokine therapy in a subject, which method comprises administering to the subject a composition comprising an effective amount of the peptide of claim 1.

31. The method of claim 30, wherein the peptide includes a linker group, or one or more non-proteogenic amino acid insertions or substitutions, or a combination thereof.

32. The method of claim 30, wherein the peptide comprises a sequence selected from the group consisting of SEQ ID NOs: 2-9.

33. The method of claim 30, wherein the peptide comprises a sequence selected from the group consisting of SEQ ID NOs: 11-16.

34. The method of claim 30, further comprising administering chemotherapy to the subject.

35. The method of claim 30, wherein the LUBAC inhibitor is a peptide inhibitor comprising any one of SEQ ID NOs: 2-16 and wherein the peptide comprises 45 amino acids or fewer in length.

36. A method of treating chronic autoinflammation, systemic lupus erythematosus, Crohn's inflammatory bowel disease, or psoriasis in a subject, which method comprises administering to the subject a composition comprising an effective amount of the peptide of claim 1.

37. The method of claim 36, wherein the peptide comprises any one of SEQ ID NOs: 2-16 and wherein the peptide comprises 45 amino acids or fewer in length.

38. The method of claim 37, wherein the peptide includes a linker group, or one or more non-proteogenic amino acid insertions or substitutions, or a combination thereof.

39. The method of claim 37, wherein the peptide comprises a sequence selected from the group consisting of SEQ ID NOs: 2-9.

40. The method of claim 37, wherein the peptide comprises a sequence selected from the group consisting of SEQ ID NOs: 11-16.

* * * * *